United States Patent
Hatzigeorgiou et al.

(10) Patent No.: US 8,532,937 B2
(45) Date of Patent: *Sep. 10, 2013

(54) METHODS AND SYSTEMS FOR IDENTIFYING MICRO-RNA TARGETS AND SYNTHESIZING NOVEL MICRO-RNAS AND USES OF THE SAME

(75) Inventors: Artemis G. Hatzigeorgiou, Philadelphlia, PA (US); Zissimos Mourelatos, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,646

(22) Filed: Feb. 22, 2012

(65) Prior Publication Data
US 2012/0244618 A1  Sep. 27, 2012

Related U.S. Application Data

(62) Division of application No. 10/564,707, filed as application No. PCT/US2004/022934 on Jul. 15, 2004, now Pat. No. 8,145,436.

(60) Provisional application No. 60/487,321, filed on Jul. 15, 2003.

(51) Int. Cl.
C07H 21/02 (2006.01)
(52) U.S. Cl.
USPC .......................................... 702/20; 536/24.5
(58) Field of Classification Search
None
See application file for complete search history.

(56) References Cited

U.S. PATENT DOCUMENTS

| | | | |
|---|---|---|---|
| 7,250,496 | B2 | 7/2007 | Bentwich |
| 7,696,342 | B1 | 4/2010 | Bentwich |
| 2004/0249178 | A1 | 12/2004 | Vargeese et al. |
| 2005/0008617 | A1 | 1/2005 | Chen et al. |
| 2006/0003322 | A1 | 1/2006 | Bentwich |

OTHER PUBLICATIONS

Doench, et al., "Specificity of microRNA target selection in translational repression", Genes Dev. Mar. 1, 2004;18 (5):504-11.
Zeng, et al, "Sequence requirements for micro RNA processing and function in human cells", RNA. Jan. 2003;9 (1):112-23.
McManus, et al., "Gene silencing using micro-RNA designed hairpins", RNA. Jun. 2002;8(6):842-50.
Abrahante et al., "The *Caenorhabditis elegans* hunchback-like Gene lin-57/hbl-I Controls Developmental Time and Is Regulated by MicroRNAs," Dev Cell 4:625-37, 2004.
Amarzguioui et al. "Tolerance for mutations and chemical modifications in a siRNA," Nucleic Acids Res 31: 589-95, 2003.
Ambros et al., "A uniform system for microRNA annotation," (2003) RNA 9:277-9.
Ambros et al., "MicroRNAs and Other Tiny Endogenous RNAs in *C. elegans*," (2003) Curr Biol 13:807-18.
Aukerman et al., "Regulation of Flowering Time and Floral Organ Identity by a MicroRNA and Its APETALA2-Like Target Genes," (2003) Plant Cell 15:2730-41.
Bartel et al., "MicroRNAs: At the Root of Plant Development?" Plant Physiol (2003) 132:709-17.
Bartel et al., "MicroRNAs: genomics, biogenesis, mechanism, and function," (2004) Cell 116:281-97.
Bernstein et al., "Role for a bidentate ribonuclease in the initiation step of RNA interference," (2001) Nature 409:363-6.
Bohnsack et al., "Exportin 5 is a RanGTP-dependent dsRNA-binding protein that mediates nuclear export of pre-miRNAs," (2004) RNA 10:185-91.
Brennecke et al., "Bantam Encodes a Developmentally Regulated microRNA that Controls Cell Proliferation and Regulates the Proapoptotic Gene hid in *Drosophila*," (2003) Cell 113:25-36.
Calin et al., "Frequent deletions and down-regulation of micro-RNA genes miR15 and miR16 at 13q14 in chronic lymphocytic leukemia," (2002) Proc Natl Acad Sci USA 99:15524-9.
Chen, "A microRNA as a translational repressor of APETALA2 in *Arabidopsis* Flower Development," (2002) Science 303:2022-25.
Doench et al., "siRNAs can function as miRNAs," (2003) Genes Dev 17:438-42.
Enright et al., "MicroRNA targets in Drosophila," (2003) Genome Biology 5(1)R1.
Dostie et al., "Numerous microRNPs in neuronal cells containing novel microRNAs," (2003) RNA 9:180-186.
Elbashir et al., "RNA interference is mediated by 21- and 22-nucleotide RNAs," (2001) Genes Dev 15:188-200.
Grishok et al., "Genes and mechanisms related to RNA interference regulate expression of the small temporal RNAs that control *C. elegans* developmental timing," (2001) Cell 106:23-34.
Hutvagner et al., "A cellular function for the RNA-interference enzyme Dicer in the maturation of the let-7 small temporal RNA," (2001) Science 293:834-8.
Hammond et al., "Argonaute2, a link between genetic and biochemical analyses of RNAi," Science (2001)293:1146-50.
Ha et al., "A bulged lin-4/lin-14 RNA duplex is sufficient for *Caenorhabditis elegans* lin-14 temporal gradient formation," (1996) Genes Dev 10:3041-50.
Hamilton et al., "A species of small antisense RNA in post-transcriptional gene silencing in plants," Science (1999.) 286:950-2.
Hutvagner et al., "A microRNA in a multiple-turnover RNAi enzyme complex," (2002) Science 297:2056-60.
Kasprzyk et al., "EnsMart: a generic system for fast and flexible access to biological data," (2004) Genome Res 14:160-9.
Kasschau et al., "PI/HC-Pro, a viral suppressor of RNA silencing, interferes with *Arabidopsis* development and miRNA unction," (2003) Dev Cell 4: 205-17.
Ketting et al., "Dicer functions in RNA interference and in synthesis of small RNA involved in developmental timing in *C. elegans*," (2001) Genes Dev 15:2654-9.

(Continued)

Primary Examiner — Richard Schnizer
(74) Attorney, Agent, or Firm — Pepper Hamilton, LLP

(57) ABSTRACT

Method of identifying a microRNA-recognition element and of generating microRNAs are disclosed. System and computer programs for performing such methods are disclosed. Recombinant nucleic acid molecule comprising a heterologous coding sequences and one or more MREs are also disclosed as are isolated nucleic acid molecule comprising one or more MRE sequences and being free of a coding sequence operably linked to regulatory elements. MicroRNA generated by a methods of the invention and the use of the microRNAs to downregulate gene expression are disclosed.

4 Claims, 12 Drawing Sheets

(56) References Cited

OTHER PUBLICATIONS

Khvorova et al., "Functional siRNAs and miRNAs exhibit strand bias," (2003) Cell 115:209-16.
Knight et al., "A role for the RNase Hi enzyme DCR-1 in RNA interference and germ line development in *Caenorhabditis elegans*," (2001) Science 293:2269-71.
Lagos-Quintana et al., "Identification of novel genes coding for small expressed RNAs," (2001) Science 294: 853-8.
Lagos-Quintana et al., "Identification of tissue-specific microRNAs from mouse," (2002) Curr Biol 12: 735-9.
Lai, "Micro RNAs are complementary to 3' UTR sequence motifs that mediate negative post-transcriptional regulation," (2002) Nat Genet 30: 363-4.
Lai et al., "Computational identification of *Drosophila* microRNA genes," (2003) 4:R42.
Lau et al., "An abundant class of tiny RNAs with probable regulatory roles in *Caenorhabditis elegans*," (2001) Science 294:858-62.
Lee et al., "An extensive class of small RNAs in *Caenorhabditis elegans*," (2001), Science 294862-4, 294:882-864.
Lee et al., "The *C. elegans* heterochronic gene lin-4 encodes small RNAs with antisense complementarity to lin-14," (1993) Cell 75:843-54.
Lee et al., "The nuclear RNase III Drosha initiates microRNA processing," (2003) Nature 425:415-9.
Lewis et al., "Prediction of mammalian microRNA targets," (2003) Cell 115:787-98.
Lim et al. "The microRNAs of *Caenorhabditis elegans*," (2003) Genes Dev 17:991-1008.
Lin et al., "The *C. elegans* hunchback Homolog, hbl-1, Controls Temporal Patterning and Is a Probable MicroRNA Target," (2003) Dev Cell 4: 639-50.
Llave et al., "Cleavage of Scarecrow-like mRNA targets directed by a class of *Arabidopsis* miRNA," (2002) Science 297:2053-6.
Lund et al., "Nuclear export of microRNA precursors," (2004) Science 303:95-8.
Martinez et al., "Single-stranded antisense siRNAs guide target RNA cleavage in RNAi," Cell 110:563-74. 2002.
Mazumder et al., "Translational control by the 3'-UTR: the ends specify the means," (2003) Trends Biochem Sci 28:91-8.
Michael et al., "Reduced accumulation of specific microRNAs in colorectal neoplasia," (2003) Mol Cancer Res 1:882-91.
Moss et al., "The cold shock domain protein LIN-28 controls developmental timing in *C. elegans* and is regulated by the linRNA," (1997), Cell, 88:637-46.
Nussinov "Nearest neighbor nucleotide patterns. Structural and biological implications," (1981) / Bid Chem 256:8458-62.
Olsen et al., "The lin-4 regulatory RNA controls developmental timing in *Caenorhabditis elegans* by blocking LIN-14 protein synthesis after the initiation of translation," (1999) Dev Biol 216: 671-80.
Palatnik et al., "Control of leaf morphogenesis by microRNAs," (2003) Nature 425:257-63.
Pesole et al., "UTRdb and UTRsite: specialized databases of sequences and functional elements of 5' and 3' untranslated regions of eukaryotic mRNAs," (2002) Nucleic Acids Res 30:335-40.
Pruitt et al., "NCBI Reference Sequence project: update and current status," (2003) Nucleic Acids Res 31:34-7.
Reinhart et al., "The 21-nucleotide let-7 RNA regulates developmental timing in *Caenorhabditis elegans*," (2000) Nature 403:901-6.
Rhoades et al., "Prediction of plant microRNA targets," (2002) Cell 110:513-20.
Schwarz et al., "Asymmetry in the assembly of the RNAi enzyme complex," (2003) Cell 115:199-208.
Seggerson et al., "Two genetic circuits repress the *Caenorhabditis elegans* heterochronic gene lin-28 after translation initiation," (2002) Dev Biol 243:215-25.
Seitz et al., "Imprinted microRNA genes transcribed antisense to a reciprocally imprinted retrotransposon-like gene," (2003) Nat Genet 34: 261-2.
Stark et al., "Identification of *Drosophila* MicroRNA Targets," (2003) Plos Biology 1:1-13.
Tang et al., "A biochemical framework for RNA silencing in plants," (2003) Genes Dev 17: 49-63.
Tinoco et al.," Improved estimation of secondary structure in ribonucleic acids," (1973) Nat New Biol 246(150):40-41.
Vella et al., "The *C. elegans* microRNA let-7 binds to imperfect let-7 complementary sites from the lin-41 3'UTR," (2004) Genes Dev 18:132-7.
Wightman et al., Posttranscriptional regulation of the heterochronic gene lin-14 by lin-4 mediates temporal pattern formation in *C. elegans*/ (1993) Cell 75:855-62.
Xie et al., "Negative Feedback Regulation of Dicer-Likel in *Arabidopsis* by microRNA-Guided mRNA Degradation," (2003) Curr Biol 13:784-9.
Xu et a;l., "The *Drosophila* MicroRNA Mir-14 Suppresses Cell Death and Is Required for Normal Fat Metabolism," (2003) Curr Biol 13:790-5.
Yi et al., "Exportin-5 mediates the nuclear export of pre-microRNAs and short hairpin RNAs," (2003) Genes Dev 17:3011-6.
Zeng et al., "Both natural and designed micro RNAs can inhibit the expression of cognate mRNAs when expressed in human cells," (2002) Mol Cell 9:1327-33.
Nelson et al., "The microRNA world: small is mighty," (2003) Trends Biochemical Science 28:534-540.
Nelson et al,. miRNP:mRNA association in polyribosomes in a human neuronal cell line. (2004) RNA 10:387-394.
Moss et al., "Conservation of the heterochronic regulator Lin-28, its developmental expression and microRNA complementary sites," (2003) Dev Biol 258:432-42.
Mourelatos et al., "miRNPs: a novel class of ribonucleoproteins containing numerous microRNAs," (2002) Genes Dev 16: 720-8.

METHODS AND SYSTEMS FOR IDENTIFYING MICRO-RNA TARGETS AND SYNTHESIZING NOVEL MICRO-RNAS AND USES OF THE SAME

CROSS-REFERENCE TO RELATED APPLICATIONS

This application is a divisional of U.S. patent application Ser. No. 10/564,707, filed on Jun. 30, 2006, pending, which claims priority to and is a national stage application under 35 U.S.C. §371 of PCT International Application Serial Number PCT/US2004/022934, filed Jul. 15, 2004, which claims priority to U.S. Provisional Patent Application Ser. No. 60/487,321, filed Jul. 15, 2003, each of which is incorporated herein by reference in its entirety.

GOVERNMENT SUPPORT

This invention was made with government support under grant number(s) NS02199, AG00255, and AR07442 awarded by National Institute of Health. The government has certain rights in the invention.

FIELD OF THE INVENTION

The present invention relates to the field of microRNA and microRNA targets. In particular, the invention relates to a computational method of predicting microRNA targets, systems for performing such a method and programs that include instructions for performing the method as well as methods of designing and synthesizing novel microRNAs, systems for performing such a method and programs that include instructions for performing the methods. The present invention relates to novel miRNAs and there uses and to novel microRNA targets and their uses.

BACKGROUND OF THE INVENTION

MicroRNAs (miRNAs) are derived from endogenous genes that are initially transcribed as longer RNA transcripts (Lee et al. 1993) (Wightman et al. 1993) (Reinhart et al. 2000) (Lagos-Quintana et al. 2001) (Lau et al. 2001) (Lee and Ambros 2001) (Mourelatos et al. 2002) (reviewed in (Nelson et al. 2003), (Bartel 2004)). In mammals, the primary miRNA transcripts (pri-miRNAs) are processed by the nuclease Drosha (Lee et al. 2003) into ~70 nt precursor miRNAs (pre-miRNAs) that are exported by exportin-5 to the cytoplasm (Yi et al. 2003; Lund et al. 2004) (Bohnsack et al. 2004). The Dicer nuclease excises the mature miRNAs from pre-miRNAs (Hutvagner et al. 2001) (Ketting et al. 2001) (Knight and Bass 2001) (Grishok et at. 2001). miRNAs are bound to proteins that belong to the Argonaute family and, in humans, may also assemble with other proteins, including the Gemin3 and Gemin4 proteins, to form micro-Ribonucleoprotein complexes (miRNPs) (Mourelatos et al. 2002) (Nelson et al. 2004). Dicer also processes another class of ~22 nt RNAs termed short interfering RNAs (siRNAs) (Elbashir et al. 200)) (Hamilton and Baulcombe 1999) from double stranded RNAs (Bernstein et al. 2001). Analogous to miRNAs, siRNAs are bound to Argonaute proteins (Hammond et al. 2001) (Martinez et al. 2002) and may also assemble with additional proteins to form RNA-induced Silencing Complexes (RISCs) (Hammond et al. 2001). siRNAs and miRNAs (and RISCs and miRNPs) are functionally equivalent and the main difference between the two classes of small RNAs are the fact that miRNAs are derived from endogenous genes (Ambros et al. 2003a).

Many miRNAs and siRNAs function by base pairing with miRNA-recognition elements (MREs) found in their mRNA targets and direct either target RNA endonucleolytic cleavage (Elbashir et al. 2001) (Hutvagner and Zamore 2002) or translational repression (Olsen and Ambros 1999; Seggerson et al. 2002; Zeng et al. 2002; Doench et al. 2003). The manner by which a miRNA or siRNA base pairs with its mRNA target correlates with its function: if the complementarity between a miRNA and its target is extensive, the RNA target is cleaved (Hutvagner and Zamore 2002) (Rhoades et al. 2002) (Llave et al. 2002) (Tang et al. 2003) (Xie et al. 2003); if the complementarity is partial, the stability of the target mRNA in not affected but its translation is repressed (Olsen and Ambros 1999; Seggerson et al. 2002; Zeng et al. 2002; Doench et al. 2003). However, how general this correlation is and the factors and mechanisms that determine the function of any given miRNA are unknown.

In plants, the computational identification of miRNA targets was facilitated by the extensive complementarity between plant miRNAs and their mRNA targets (Llave et al. 2002). (Rhoades et al. 2002). Plant miRNA targets have been verified experimentally (Llave et al. 2002) (Xie et al. 2003) (Kasschau et al. 2003) (Palatnik et al. 2003) (Aukerman and Sakai 2003) (Chen 2004) reviewed in (Bartel and Bartel 2003). Two mouse miRNAs (miR-127 and miR-136) show perfect antisense complementarity with the coding region of a retrotransposon-like gene (Rtl1) (Seitz et al. 2003). However, most animal miRNAs are thought to recognize their mRNA targets via partial antisense complementarity (Lee et al. 1993) (Wightman et al. 1993) (Moss et al. 1997) (Reinhart et al. 2000) (Olsen and Ambros 1999; Zeng et al. 2002; Doench et al. 2003). Because of this partial complementarity, simple homology-based searches have failed to uncover targets for miRNAs in organisms other than plants (Bartel and Bartel 2003) (Ambros et al. 2003b). Animal miRNA targets were initially identified in genetic screens. In particular, genetic dissection of the heterochronic gene pathway in *C. elegans* identified the lin-14 and lin-28 mRNAs as targets for the lin-4 miRNA (Lee et al. 1993) (Wightman et al. 1993) (Moss et al. 1997), and the lin-41 mRNA as a target for the let-7 miRNA (Reinhart et al. 2000). In *Drosophila*, the bantam miRNA regulates the pro-apoptotic gene hid (Brennecke et al. 2003). Importantly, these and other studies demonstrated that MRE sequences are necessary and sufficient to confer miRNA-dependent gene expression regulation in MRE-bearing target mRNAs (Moss et al. 1997) (Reinhart et al. 2000) (Zeng et a). 2002) (Doench et al. 2003) (Vella et al. 2004). Putative targets for other miRNAs have been proposed (Lai 2002; Abrahante J E 2003; Lin S Y 2003; Xu et al. 2003), but these are predominantly based on visual inspection of putative mRNA targets for partial complementarity with miRNAs and lack experimental verification of specific miRNA:MRE interactions.

Very recently, carefully designed bioinformatic approaches have been used to predict mRNA targets for *Drosophila* (Stark et al. 2003) (Enright et al. 2003) and mammalian miRNAs (Lewis et al. 2003). In particular, Bartel, Burge and colleagues have presented a robust bioinformatics strategy that allows prediction of conserved, mammalian miRNA targets along with accurate estimates of false positive rates (at 31% for miRNA targets identified in human mouse and rat and 22% for targets identified in mammals and in pufferfish) and experimental validation of 11 (out of 15 tested) predicted targets (Lewis et al. 2003). Most of the targets identified by Lewis et al. contain multiple MREs for the same miRNA or are regulated by more that one miRNA. The targets reported for *Drosophila* miRNAs also contain, for the most part, multiple MREs (Stark et al. 2003) (Enright et al. 2003). However, the rules guiding single miRNA:MRE (target mRNA) interactions have not been investigated and as a result predictions of miRNA targets containing single MREs are lacking.

There remains a need for an algorithm providing rules that guide single miRNA:MRE (target mRNA) recognition. There remains a need for methods, systems and computer programs which use the rules to identify MREs.

SUMMARY OF THE INVENTION

The present invention relates to methods of identifying a microRNA-recognition element. According to the methods, the degree of complementarity of a microRNA nucleotide sequence to an mRNA sequence is compared to identify the presence of an mRNA sequence that exhibits a degree of complementarity to the microRNA sequence that is indicative of a microRNA-recognition element for the microRNA according to certain binding rules set forth herein.

The present invention also relates to system for identifying a microRNA-recognition element and computer programs embodied on a computer readable medium for implementation on a computer system that for identifying a microRNA-recognition element using instructions according to the method of identifying a microRNA-recognition element.

The present invention further relates to method of generating microRNAs. The methods comprise identifying a selected mRNA sequence to be the target of the microRNA and generating an oligonucleotide sequences that is 17-25 nucleotides and has a degree of complementarity to the selected mRNA sequence that is indicative of a microRNA—recognition element for a microRNA that said mRNA sequence is a microRNA-recognition element for the microRNA, wherein the selected mRNA sequence is in the 3' untranslated region of an mRNA; wherein the microRNA includes a proximal region that is 7-9 nucleotides, has a 5' end and a 3' end and includes a nucleotide at the 5' end which is the microRNA's 5' terminus nucleotide, a distal region thai is 7-15 nucleotides, has a 5' end and a 3' end and includes a nucleotide at the 3' end which is the microRNA's 3' terminus nucleotide, and a loop region that is 0 nucleotide. 2-3 nucleotides or 6-9 nucleotide, wherein when the loop region is 0 nucleotides the 3' end of the proximal region is contiguous to the 5' end of the distal region and when the loop region is 2-3 or 6-9 nucleotides the 3' end of the proximal region is contiguous to the 5' end of the loop region and the 3' end of the loop region is contiguous to the 5' end of the distal region, wherein complementarity of the mRNA sequence to the microRNA sequence that is indicative of a microRNA-responsc element for the microRNA is characterized by: the mRNA sequence having a sequence that: a) includes a region corresponding to the proximal region of the microRNA that is either completely complementary to the proximal region, or has a single mismatch to the 5' end of the proximal region, or symmetrically placed between the 5' end of the proximal region and the 3' end of the proximal region; b) includes a region corresponding to the loop region of the microRNA that either forms a loop of 2-5 non-paired nucleotides when the loop region is 0, or has 0 nucleotides when the loop region is 6-9 nucleotides, or has 2-3 nucleotides which forms a bulge of 2-3 non-complementary nucleotides of the loop region when the loop region is 2-3 nucleotides; and c) includes a region corresponding to the distal region that is either completely complementary to at least 7 contiguous nucleotides of the distal region including the 5' end of the distal region, or contains mismatches of 1-4 contiguous nucleotides and matches of at least 5 nucleotides to a contiguous nucleotide sequence of the distal region including the 5' end of the distal region; wherein the oligonucleotide sequence has a degree of complementarity to the selected mRNA sequence that is indicative of a microRNA for a microRNA-rccognition element. The method may further comprising the step of determining free energy of the microRNA bound to the selected mRNA sequence wherein a free energy determination of −10 kcal/mole or less indicates that said mRNA sequence is a microRNA-recognition element for the microRNA. In the method, a free energy determination of −20 kcal/mole or less, or −30 kcal/mole or less, indicates that said mRNA sequence is a microRNA-recognition element for the microRNA.

The present invention also relates to system for generating a microRNA and computer programs embodied on a computer readable medium for implementation on a computer system that for generating a microRNA using instructions according to the method of identifying a microRNA-recognition element.

Additional aspects of the invention relates to recombinant nucleic acid molecule comprising a heterologous coding sequences and one or more MREs identified by the methods of the invention and as well as isolated nucleic acid molecule free of a coding sequence operably linked to regulatory elements and comprising one or more MRE sequences identified by such methods.

The invention further relates to microRNA generated by a methods of the invention and methods of using microRNA generated by a methods of the invention to down regulate expression of an mRNA.

BRIEF DESCRIPTION OF THE DRAWINGS

FIG. 1A shows a schematic representation of the reporter construct; red: coding region. FIG. 1B shows potential base pairing between predicted MREs derived from the indicated mRNAs and their cognate miRNAs (blue); wt: wild-type sequence. MRE sequences that repressed the expression of luciferase are shown in green while the sequences that did not are shown in red. The sequence identified as LIN-41a is SEQ ID NO:1. The sequence identified as let-7a is SEQ ID NO:2. The sequence identified as LIN-41b is SEQ ID NO:3. The sequence identified as LIN-28, wt is SEQ ID NO:4. The sequence identified as let-7b is SEQ ID NO:5. The sequence identified as LIN-28,M1 is SEQ ID NO:6. The sequence identified as LIN-28, M2 is SEQ ID NO:7. The sequence identified as LIN-28, M3 is SEQ ID NO:8. The sequence identified as LIN-28, M4 is SEQ ID NO:9. The sequence identified as LIN-28, M5 is SEQ ID NO:10. The sequence identified as LIN-28, M6 is SEQ ID NO:11. The sequence identified as LIN-28,M7 is SEQ ID NO:12. The sequence identified as LIN-28, M8 is SEQ ID NO:13. The sequence identified as LIN-28, M9 is SEQ ID NO:14. The sequence identified as LIN-28, M10 is SEQ ID NO:15. The sequence identified as LIN-28, M11 is SEQ ID NO:16. The sequence identified as LIN-28, M12 is SEQ ID NO:17. The sequence identified as LIN-28, M13 is SEQ ID NO:18. The sequence identified as LIN-29, M14 is SEQ ID NO:19. The sequence identified as LIN-28, M15 is SEQ ID NO:20. The sequence identified as LIN-28, M16 is SEQ ID NO:21. The sequence identified as LIN-28, M17 is SEQ ID NO:22. The sequence identified as LIN-28, M18 is SEQ ID NO:23. The sequence identified as LIN-28, M19 is SEQ ID NO:24. The sequence identified as LIN-28, M20 is SEQ ID NO:25. The sequence identified as LIN-28, M21 is SEQ ID NO:26. FIG. 1C shows data from HeLa human cells (black bars) or MN-1 mouse cells (gray bars) that were cotransfected with Renilla Luciferase (RL) constructs bearing the indicated MREs in the 3'-UTR, along with Firefly Luciferase (FL). Results shown are average values (with standard deviations) of normalized RL/FL activities obtained from six separate experiments. FIG. 1D shows data from HeLa cells that were transfected with indicated constructs, total RNA was isolated and RL and βactin (as a normalization control) mRNAs were visualized with Northern blots.

FIG. 2A shows potential base pairing between LIN-28 MREs and endogenous let-7b or synthetic let-7b siRNAs. Mutated nucleotides are shown. The sequence identified as Let-7b-M1 is SEQ ID NO:27. The sequence identified as Let-7b-M4 is SEQ ID NO:28. FIG. 2B and 2C show data from Hela cells that were cotransfected with Renilla Luciferase (RL) constructs bearing the indicated MREs in the 3'-UTR, along with Firefly Luciferase (FL) and with or without the indicated synthetic siRNAs (30 nM). Results shown are average values (with standard deviations) of normalized RL/FL activities obtained from three separate experiments.

FIG. 3A shows potential base pairing between predicted MREs derived from the indicated mRNAs and their cognate miR-NAs. Numbers refer to nucleotide positions after the stop codon, based on the human mRNAs. The sequence identified as CLOCK is SEQ ID NO:29. The sequence identified as miR-141 is SEQ ID NO:30. The sequence identified as MAPK14 is SEQ ID NO:31. The sequence identified as miR-24 is SEQ ID NO:32. FIG. 3B shows HeLa (black bars) or MN-1 (gray bars) cells were cotransfected with Renilla Luciferase (RL) constructs bearing the indicated MREs in the 3'-UTR, along with Firefly Luciferase (FL). Results shown are average values (with standard deviations) of normalized RL/FL activities obtained from six separate experiments.

FIG. 5A shows a schematic representation of miRNA:MRE (target mRNA) bindings (miRNA binding rules). P refers to the proximal (relative to 5'-end of miRNA) region of miRNA:MRE binding; D refers to the distal region of binding. Structure α shows the loop region of the miRNA and the corresponding region on the MRE to have a length on each sequence of 2 to 3 nucleotides. Structure β contains a single MRE central bulge in which the loop region of the miRNA has 0 nucleotides and the region of the MRE corresponding to the loop region of the miRNA has nucleotides forming loop having the length of 2 to 5 unpaired nucleotides. Structure γ contains a single miRNA central bulge in which the loop region of the miRNA has 6-9 nucleotides and the region of the MRE corresponding to the loop region of the miRNA has 0 nucleotides such that the miRNA loop region has 6 to 9 unpaired nucleotides. Proximal binding characteristics show that ≧7 nucleotide base pairing between miRNA and MRE is required; the 5' most nucleotide of the miRNA may or may not base pair with MRE; one symmetric single nucleotide bulge allowed (i.e. the single nucleotide bulge is surrounded by an equal number of base-paired nucleotides). Distal binding characteristics show that ≧5 nucleotide base pairing between miRNA and MRE; nucleotide bulges allowed. The last (towards the 3'-end) nucleotides of the miRNA may or may not base pair with the MRE. FIG. 4 shows hits between 10 human miRNAs (left bar of pairing) or shuffled RNAs (right bar of pairing) and the 3'-UTR database of annotated human mRNAs or the conserved human/mouse 3'-UTR database (initial analysis). FIG. 4 shows hits between 94 human miRNAs (left bar) or shuffled controls (with the same compositional properties as the authentic miRNAs; right bar) and the conserved human/mouse 3'-UTR database extracted using EnsMart.

In FIG. 6A, the sequence identified as FLJ21308 is SEQ ID NO:55. The sequence identified as miR-145 is SEQ ID NO:56. The sequence identified as FLJ13158 is SEQ ID NO:57. The sequence identified as miR-23a is SEQ ID NO:58. The sequence identified as SMC1L1 is SEQ ID NO:59. The sequence identified as let-7e is SEQ ID NO:60. The sequence identified as hDMP1 is SEQ ID NO:61. The sequence identified as miR-15 is SEQ ID NO:62. The sequence identified as CGI-38 is SEQ ID NO:63. The sequence identified as miR-16 is SEQ ID NO:64. The sequence identified as LAMC2 is SEQ ID NO:65. The sequence identified as miR-199b is SEQ ID NO:66. The sequence identified as FBXW1B is SEQ ID NO:67. The sequence identified as miR-103-1 is SEQ ID NO:68. The sequence identified as LIN-28, M29 is SEQ ID NO:69.

DETAILED DESCRIPTION OF PREFERRED EMBODIMENTS

Definitions

Figure 1A:
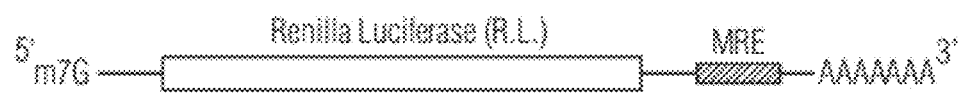
FIGS. 1A, 1B, 1C, and 1D disclose experimental verification of a predicted miRNA recognition element (MRE) and deduction of the miRNA Binding Rules.

As used herein, the term "degree of complementarity" refers to the pattern of complementary nucleotides, mismatched nucleotides and nucleotide bulges between two nucleic acid sequences compared with one sequence 5'-3' versus the other sequence 3'-5' (e.g. sense versus antisense).

As used herein, the term "proximal region of a microRNA" refers to the sequence of 7-9 contiguous nucleotides starting from and including the 5' terminus of the microRNA.

As used herein, the term "5' end of the proximal region" refers to the nucleotide at the 5' terminus of the microRNA.

As used herein, the term "3' end of the proximal region" refers to the nucleotide which is either the $7^{th}$ nucleotide in a nucleotide sequence of 7 contiguous nucleotides that make up a proximal region of a microRNA that is 7 nucleotides in length, the $8^{th}$ nucleotide in a nucleotide sequence of 8 contiguous nucleotides that make up a proximal region of a microRNA that is 8 nucleotides in length or the $9^{th}$ nucleotide in a nucleotide sequence of 9 contiguous nucleotides that make up a proximal region of a microRNA that is 9 nucleotides in length wherein the nucleotide at the 3' end of the proximal region is contiguous with either the nucleotide of the 5' end of the loop region unless the loop region is 0 nucleotides in which case the 3' end of the proximal region is contiguous with the nucleotide of the 5' end of the distal region.

As used herein, the term "loop region of a microRNA" refers to the sequence of 0, 2-3 or 6-9 contiguous nucleotides starting at and including the nucleotide contiguous to the 3' end of the proximal region and ending at the nucleotide contiguous with the 5' end of the distal region wherein when the loop region is 0 nucleotides, the 3' end of the proximal region is contiguous with either the nucleotide of the 5' end of the distal region.

As used herein, the term "distal region of a microRNA" refers to the sequence of 7-15 contiguous nucleotides including the nucleotide at the 3' terminus of the microRNA.

As used herein, the term "5' end of the distal region" refers to the nucleotide which is either the $7^{th}$ nucleotide upstream from the nucleotide at the 3' terminus in a distal region of a microRNA that is 7 nucleotides in length, the $8^{th}$ nucleotide upstream from the nucleotide at the 3' terminus in a distal region of a microRNA that is 8 nucleotides in length, the $9^{th}$ nucleotide upstream from the nucleotide at the 3' terminus in a distal region of a microRNA that is 9 nucleotides in length, the $9^{th}$ nucleotide upstream from the nucleotide at the 3' terminus in a distal region of a microRNA that is 9 nucleotides in length, the $10^{th}$ nucleotide upstream from the nucleotide at the 3' terminus in a distal region of a microRNA that is 10 nucleotides in length, the $10^{th}$ nucleotide upstream from the nucleotide at the 3' terminus in a distal region of a microRNA that is 10 nucleotides in length, the $11^{th}$ nucleotide upstream from the nucleotide at the 3' terminus in a distal region of a microRNA that is 11 nucleotides in length, the $12^{th}$ nucleotide upstream from the nucleotide at the 3' terminus in a distal region of a microRNA that is 12 nucleotides in length, the $13^{th}$ nucleotide upstream from the nucleotide at the 3' terminus in a distal region of a microRNA that is 13 nucleotides in length, the $14^{th}$ nucleotide upstream from the nucleotide at the 3' terminus in a distal region of a microRNA that is 14 nucleotides in length, or the $15^{th}$ nucleotide upstream from the nucleotide at the 3' terminus in a distal region of a microRNA that is 15 nucleotides in length, wherein the nucleotide at the 5' end of the distal region is contiguous with either the nucleotide of the 3' end of the loop region unless the loop region is 0 nucleotides in which case the 5' end of the distal region is contiguous with the nucleotide of the 3' end of the distal region.

As used herein, the term "3' end of the distal region" refers to the nucleotide at the 3' terminus of the microRNA.

As used herein, the term "degree of complementarity of the mRNA sequence to the microRNA sequence that is indicative of a microRNA-response element for the microRNA" refers to the pattern of complementary nucleotides, mismatched nucleotides and nucleotide bulges between a 5'-3' mRNA sequence and a 3'-5' microRNA sequence that is consistent with the patterns when the mRNA sequence is the microRNA-response element for the microRNA.

As used herein the term "mismatch" refers to either a nucleotide of either an miRNA or MRE having no corresponding nucleotide on the corresponding MRE or miRNA or a nucleotide of either an miRNA or MRE having a corresponding nucleotide on the corresponding MRE or miRNA that is non-complementary.

As used herein, a "match" refers to a complementary pairing of nucleotides.

As used herein, the term "bulge" refers to non-complementarity between two sequences that contain complementary sequences. A bulge arises from one or more nucleotides of a miRNA or MRE sequence with no nucleotide on the corresponding MRE or miRNA on the other and having pairs of complementary nucleotides on either side and/or from one or more non-complementary pair of nucleotides having complementary base pairs on either side unless the bulge contains either a nucleotide of the 5' or 3' termini. Thus, a bulge can arise from a combination of one or more non-complementary pair and one or more one or more nucleotides of a miRNA or MRE sequence with no nucleotide on the corresponding MRE or miRNA. Accordingly, the bulge may include 0-4 nucleotides on a miRNA sequence being non-complementary with 0-4 nucleotides on the corresponding MRE including nucleotides one or more nucleotides of a miRNA or MRE sequence with no nucleotide on the corresponding MRE or miRNA on the other such that the bulge may arise from different numbers of nucleotides on the miRNA and corresponding MRE. A bulge arises from one or more contiguous mismatches.

As used herein, the term "region corresponding to the proximal region of the microRNA" refers to the region of an mRNA that is either completely complementary to the proximal region or has a single mismatch. The mismatch may either be at the 5' end of the proximal region or symmetrically placed between the 5' end of the proximal region and the 3' end of the proximal region.

As used herein, the term "region corresponding to the loop region of the microRNA" refers to the region of an mRNA that is between the region corresponding to the proximal region of the microRNA and the region corresponding to the distal region of the microRNA. When the loop region of a microRNA is 0, the region corresponding to the loop region of the microRNA can be a 2-5 contiguous nucleotides that form a loop of unpaired nucleotides. When the loop region of a microRNA is 6-9 nucleotides, the region corresponding to the loop region of the microRNA is 0 nucleotides and the region corresponding to the proximal region of the microRNA is contiguous with the region corresponding to the distal region of the microRNA. When the loop region of a microRNA is 2-3 nucleotides, the region corresponding to the loop region of the microRNA can have 2-3 nucleotides that are non-complementary to the nucleotides of the loop region of a microRNA so as to form a bulge.

As used herein, the term "region corresponding to the distal region of the microRNA" refers to the region of an mRNA that is either completely complementary to at least 7 contiguous nucleotides of the distal region including the 5' end of the distal region, or contains matches of at least 5 nucleotides of the distal region including the 5' end of the distal region and up to 2-3 contiguous mismatches before the 3' end of the distal region and/or up to 8 contiguous mismatches at the 3' end of the distal region.

As used herein, "determining free energy of microRNA bound to said mRNA sequence" refers to any means to ascertain the free energy including, but not limited to direct measurement, calculation using an algorithm or formula, or reference to previously measured or calculated values.

As used herein, the term "link for connecting to data or a database" refers to any connection device or system that is capable of connecting to and allows for data to be transferred transmitted or otherwise delivered from a remote data interface, a data storage device or a database directly or indirectly to a processor, data storage or data access device.

As used herein, "synthetic miRNA" refers to RNAs that do not exist in nature or where not known prior to the present invention.

As used herein, the term "generating miRNAs" refers to the process of generating a nucleotide sequence that is referred to as miRNA. In some embodiments, the generating is done in silico. Generating an miRNA sequence refers to the creation of a sequence that can bind to an MRE, not the actual synthesis of the miRNA. As discussed above, in some embodiments, the sequence that is generated is also synthesized.

miRNA Binding Rules

The present invention provides methods, systems and programs for identifying sequences within an mRNA sequence that interact with and are affected by microRNA and for designing and synthesizing synthetic miRNAs. An algorithm is provided for comparing sequence data of a miRNA and an mRNA sequence to identify patterns of complementary sequences and non-complementary sequences. The use of the algorithm together with a determination of free energy between such sequences allows for the identification of MREs. The algorithm also allows for miRNA sequences to be predicted based upon mRNA sequences. Thus, synthetic miRNAs may be designed and prepared to bind to specific mRNA sequences, making such mRNA sequences MREs for the new miRNA. The use of MREs and synthetic miRNAs are also aspects of the present invention.

According to the invention, an miRNA can be divided into 3 regions: proximal, loop and distal. It contains nucleotide sequences in at least the proximal and distal regions and may include nucleotides that for a loop region between the two. It has been discovered that in order for an mRNA sequence to be an effective MRE, a high degree of complementary base pairs is required in the proximal region. The size of loop region of an miRNA dictates the size the corresponding region on an mRNA sequence that is an MRE. There can be significantly more unpaired nucleotides, whether they be mismatches or bulges, between the distal region of an miRNA and the region on the mRNA that corresponds to the distal region in an MRE.

With respect to the degree of complementarity between the proximal region of the miRNA and the region on the mRNA that corresponds to the proximal region, the proximal region of the miRNA is either completely complementary to the region on the mRNA that corresponds to the proximal region (100% complementary sequences) or it can contain a single mismatch provided the mismatch is at a specific location. The mismatch can occur between the nucleotide at the 5' end of the miRNA or it can occur in the center of the proximal region to provide symmetrical size sequences on either size of the mismatch. That is if the miRNA proximal region is 7 nucleotides, the $4^{th}$ nucleotide can be a mismatch such that nucleotides 1-3 and 5-7 are complementary with a nucleotides of a sequence on the mRNA. If the miRNA proximal region is 8 nucleotides, the nucleotides 1-4 and 5-8 are complementary with nucleotides of a sequence on the mRNA that contains an extra nucleotide between the nucleotide complementary to nucleotide 4 and the nucleotide complementary to nucleotide 8. If the miRNA proximal region is 9 nucleotides, the $5^{th}$ nucleotide can be a mismatch such that nucleotides 1-4 and 5-8 are complementary with nucleotides of a sequence on the mRNA.

Figure 5A:
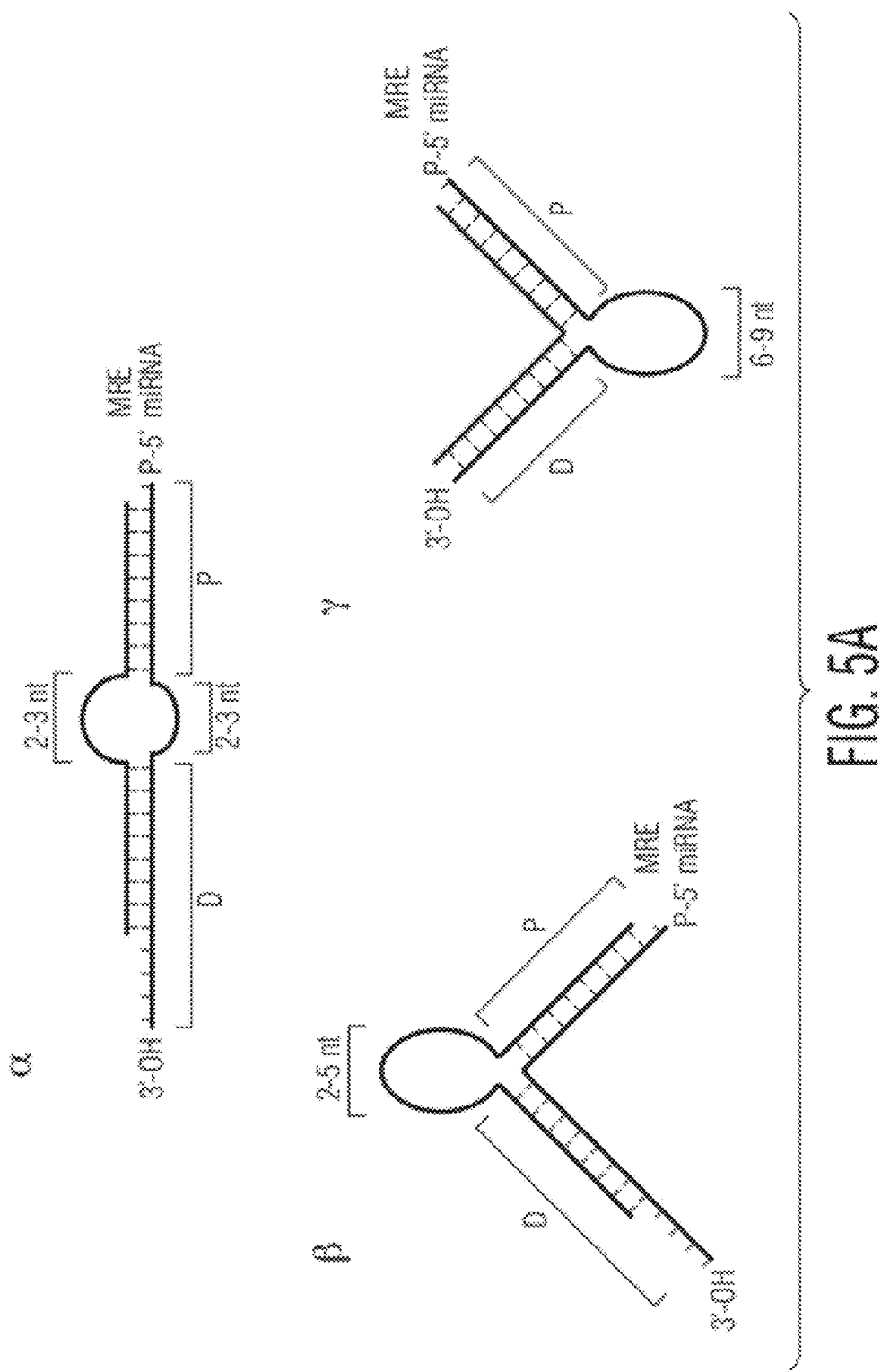
FIGS. 5A, 5B, and 5C depict MicroRNA Binding Rules and Statistics.

The degree of complementarity between miRNAs and MREs at the loop region can take several forms, which are shown in FIG. 5A. In some structures, the miRNA has no loop region but the MRE has a loop of unpaired nucleotides numbering 2-5. Thus the loop arises from the MRE sequences only and the proximal and distal regions of the miRNA are contiguous with no nucleotides where the loop region would be. In other examples, the miRNA has a loop region of 6-9 nucleotides but the MRE has no nucleotides making up a region corresponding to the loop region of the miRNA. Thus the loop arises from the miRNA sequences only and the sequences of the MRE corresponding to the proximal and distal regions of the miRNA are contiguous with no nucleotides in the region corresponding to the loop region. In still other examples, a bulge is formed such as when the miRNA has a loop region of 2-3 and the MRE has a region corresponding to is with 2-3 nucleotides. In such cases, the miRNA loop region may or may not have the same number of nucleotides as the MRE region on the mRNA that corresponds to the loop region.

The rules regarding degree of complementarity between the distal region of the miRNA and region of the MRE corresponding to it allow for a lower proportion of nucleotides required to be complementary relative to the proximal region. The distal region of the miRNA and region of the MRE corresponding to it generally have at least 5 pairs of complementary nucleotides although not necessarily all contiguous. In some embodiments, there can be one or two bulges involving 2-4 nucleotides with complementary sequences on each side. In some cases, as many as the last 8 nucleotides of an miRNA are not complementary to sequences on the mRNA.

In some embodiments, the mRNA sequences that contain the regions corresponding to the proximal loop and distal regions is in the 3' untranslated region of the mRNA. In some embodiments, the mRNA sequences that contains the regions corresponding to the proximal loop and distal regions is in the coding region of the mRNA. In some embodiments, the mRNA sequences that contains the regions corresponding to the proximal loop and distal regions is in the 5' untranslated region of the mRNA.

Free Energy

In addition to complementarity, the other component in identifying whether a sequence is an MRE relates to the amount of free energy with respect to the miRNA bound to the MRE. Generally, the free energy of a pairing of miRNA and putative MRE must be at least −10 kcal/mole. In some embodiments, it is at least −20 kcal/mole. In some embodiments, it is at least −30 kcal/mole. In the case of free energy, the negative sign (−) conveys that the energy is released. Accordingly, −20 kcal is greater than −10 kcal and thus a miRNA:MRE pairing having −20 kcal/mole has at least −10 kcal/mole.

Free energy may be determined routinely by any number of well known methods or widely available information. In some embodiments, the free energy is calculated based upon the complementary and non-complementary features of the sequence comparison using an algorithm. In some embodiments, the free energy is determined experimentally by direct measurement. In some embodiments, the free energy is determined by reference to known values.

Identifying MREs

According to the methods of the invention, the MRE is identified by taking into account whether or not the degree of complementarity between an miRNA sequence and an mRNA abide by the miRNA binding rules and whether the free energy is at least the threshold being applied, for example at least −10 kcal/mole. The order in which the two criteria are resolved is not important and determinations may be done in either order. In some cases, miRNA sequences may be scanned against mRNA sequences to first identify sequences that abide by the rules and then a free energy determination is made. In some cases, miRNA sequences may be scanned against mRNA sequences to first identify sequences that comply with the free energy requirements and then a determination is made as to whether the sequences abide by the rules. In some embodiments, the scanning is done to the 3' untranslated region of the mRNA. In some embodiments, the scanning is done to the coding region of the mRNA. In some embodiments, the scanning is done to the 5' untranslated region of the mRNA. In some embodiments, certain motifs are filtered out of the mRNA sequence data before it is used in comparisons with miRNA sequences. In some embodiments, repetitive Alu sequences are filtered out of the mRNA sequence data before it is used in comparisons with miRNA sequences.

Generating and Synthesizing Novel miRNAs

Identifying nucleotide sequences that can function as miRNAs is useful to create new tools and compounds that can be used to modulate the expression of a particular gene. The present invention can also provide methods for designing and synthesizing miRNA sequences. Accordingly, the present invention also provides for methods of identifying and/or generating miRNAs based on the micro RNA recognition element (MRE) that can be identified using the steps outlined herein. In some embodiments, the method comprises: 1) identifying an microRNA recognition element using the steps described above; 2) generating an miRNA sequence based upon the micro RNA recognition element that abides by the rules described herein; and optionally 3) synthesizing an oligonucleotide comprising the miRNA sequence that was generated in step 2. The synthesized miRNA may be tested to determine its activity.

Thus, by using the steps and methods described herein one can create novel miRNAs that can be used to modulate the expression of any gene that is transcribed into mRNA. In some embodiments, the method comprises identifying an MRE using the steps described above. Once an MRE has been identified a miRNA sequence can be generated based on the rules described above. In some embodiments, the proximal and distal regions of the miRNA is about 100%, about 99%, about 98%, about 97%, about 96%, about 95%, about 94%, about 93%, about 92%, about 91%, about 90%, about 80%, about 75%, about 70% identical to the MRE. In some embodiment the miRNA is about 10 to about 50, about 10 to about 40, about 20 to about 35, about 21, about 22, about 23, about 24, about 25 about 26, about 27, about 28, about 29, about 30, about 31, about 32, about 33, about 34, about 35 nucleobases in length.

In some embodiments, the method of identifying and/or creating miRNAs further comprises synthesizing the miRNA. Techniques for synthesizing miRNAs are known to one of ordinary skill in the art.

In some embodiments, the miRNAs comprise modified nucleobases, modified sugars, or modified linkages. Examples of modified linkages include, but not limited to, phosphorothioate linkages.

In some embodiments, the miRNA sequence has a free energy when paired with the putative MRE that is at least −10 kcal/mole, in some embodiments at least −20 kcal/mole and in some embodiments at least −30 kcal/mole.

The present invention also provides methods of generating an miRNA sequence comprising: 1) selecting an mRNA sequence that is at least 22 nucleotides in length; and 2) generating an miRNA sequence that has degree of complementarity of the mRNA sequence to the microRNA sequence that is indicative of a microRNA-response element for the microRNA. That is, using the selected mRNA sequence, an oligonucleotide is generated which has a proximal region, a distal region and forms a structure such as one of those of FIG. 5A to generate a bulge between the proximal and distal regions and/or between the region corresponding to the proximal region and the region corresponding to the distal region. The present invention can be used to identify and generate an miRNA for any sequence of mRNA that is at least 22 nucleobases in length. In some embodiments, the mRNA is at least 22, at least 23, at least 24, at least 25, at least 26, at least 27, at least 28, at least 29, at least 30, at least 31, at least 32, at least 33, at least 34, at least 35, at least 50, at least 100 nucleobases in length. In some embodiments, the mRNA is 22, 23, 24, 25, 26, 27, 28, 29, 30, 31, 32, 33, 34, 35, 50, or 100 nucleobases in length.

Once a sequence is chosen an miRNA is generated based on the rules described herein so that the miRNA is able to bind to the mRNA sequence. In some embodiments, when the miRNA binds to the mRNA the miRNA comprises a loop of 6-9 nucleotides. In some embodiments, when the miRNA binds to the mRNA, the MRE within the mRNA comprises a loop of about 2-5 nucleotides. In some embodiments, when the miRNA binds to the MRE within the mRNA, both the miRNA and the MRE comprises bulges and/or loops of 2-5 nucleobases in length.

In some embodiments, the miRNA comprises a proximal region that is 7-9 nucleotides, has a 5' end and a 3' end and includes a nucleotide at the 5' end which is the microRNA's 5' terminus nucleotide, a distal region that is 7-15 nucleotides, has a 5' end and a 3' end and includes a nucleotide at the 3' end which is the microRNA's 3' terminus nucleotide, and a loop region that is 0 nucleotide, 2-3 nucleotides or 6-9 nucleotide, wherein when the loop region is 0 nucleotides the 3' end of the proximal region is contiguous to the 5' end of the distal region and when the loop region is 2-3 or 6-9 nucleotides the 3' end of the proximal region is contiguous to the 5' end of the loop region and the 3' end of the loop region is contiguous to the 5' end of the distal region.

In some embodiments, the mRNA containing the MRE that binds to the miRNA comprises a region corresponding to the proximal region of the microRNA that is either completely complementary to the proximal region, or has a single mismatch to the 5' end of the proximal region, or symmetrically placed between the 5' end of the proximal region and the 3' end of the proximal region; a region corresponding to the loop region of the microRNA that either forms a loop of 2-5 non-paired nucleotides when the loop region is 0, or has 0 nucleotides when the loop region is 6-9 nucleotides, or has 2-3 nucleotides which forms a bulge of 2-3 non-complementary nucleotides of the loop region when the loop region is 2-3 nucleotides; and a region corresponding to the distal region that is either completely complementary to at least 7 contiguous nucleotides of the distal region including the 5' end of the distal region, or contains matches of at least 5 nucleotides of the distal region including the 5' end of the distal region and up to 2-3 contiguous mismatches before the 3' end of the distal region and/or up to 8 contiguous mismatches at the 3' end of the distal region.

In some embodiments, the miRNA binds to the mRNA with a free energy of at least −10 kcal/mole, in some embodiments at least −20 kcal/mole and in some embodiments at least −30 kcal/mole.

In some embodiments, the miRNA that is generated is synthesized and/or tested to determine if it modulates the expression of the mRNA. Testing can be done to determine whether or not the miRNA that is generated by the methods described herein modulate the expression of the mRNA. In some embodiments, the miRNA is tested and found to inhibit the expression of the mRNA. As used herein, the term "expression of the mRNA" refers to the amount of mRNA present. Therefore, if the miRNA inhibits the expression of the mRNA it can decrease the amount of the mRNA. "Expression of mRNA" can also refer to the amount of protein that is translated from a mRNA. Thus, if expression of mRNA is inhibited it can refer to a decrease in the amount of a protein that is translated from the mRNA that is inhibited. Thus, "expression of mRNA" refers to both amount (e.g. stability) and function (e.g. translation) of the mRNA. In some embodiments, the expression of the mRNA is modulated (e.g. activated or inhibited) by at least 10%, at least 20%, at least 30%, at least 40%, at least 50%, at least 60%, at least 70%, at least 80%, at least 90%, at least 95%, at least 96%, or at least 99%. In some embodiments, the expression of the mRNA is modulated (e.g. activated or inhibited) by 10%, 20%, 30%, 40%, 50%, 60%, 70%, 80%, 90%, 95%, 96%, 97%, 98%, 99%, or 100%.

Any method can be used to test miRNA including both in vitro and in vivo methods. Methods of testing miRNA are known to those of ordinary skill in the art.

In some embodiments, the selected mRNA sequence is a known MRE. In some embodiments, the selected mRNA sequence is a sequence in the 3' untranslated region of the mRNA. In some embodiments, the selected mRNA sequence is a sequence in the coding region of the mRNA. In some embodiments, the selected mRNA sequence is a sequence in the 5' untranslated region of the mRNA.

Systems and Programs for Practicing the Methods of the Invention

The method of the invention may be practiced using systems that have been programmed with instructions for performing the methods. In methods of identifying MREs, the program contains instructions for doing sequence complementary comparisons and determining whether or not sequences of mRNA and miRNA abide by the miRNA binding rules. In methods of generating novel miRNAs, the program contains instructions for designing oligonucleotides which have a degree of complementarity to a selected mRNA sequences such that the oligonucleotide is a miRNA.

In some embodiments of the invention, systems and programs are provided for identifying MREs, The systems includes a processor that contains instructions for comparing miRNA sequences to mRNA sequences to determine whether or not a given sequence of mRNA abides by the microRNA binding rules relative to the miRNA sequence. The processor receives input of miRNA and mRNA sequence information. The input may be in the form of an interface for inputting the sequence data or a database linked to the processor or a link that connects the processor to either an input interface or database. In some preferred embodiments, the miRNA is inputted into the processor through a user interface and the mRNA data is provided from a database. The system could be adapted to be connected to the internet such that the processor can connect to the database via the internet. In some embodiments, the system is adapted to be connected to the internet such that a user accesses the processor and inputs data through an internet link. In some embodiments, the system includes instructions for determining the free energy of the miRNA:mRNA pairing.

In some embodiments of the invention, systems and programs are provided for generating novel miRNAs. The systems includes a processor that contains instructions for generating an oligonucleotide sequence that abides by the miRNA:MRE binding rules for a selected mRNA sequence. The processor receives input of selected mRNA sequence information. The input may be in the form of an interface for inputting the sequence data or a database linked to the processor or a link that connects the processor to either an input interface or database. The miRNA sequence generated by the processor is provided as output. In some preferred embodiments, the mRNA sequence is inputted into the processor through a user interface. In some embodiments, the system is adapted to be connected to the internet such that a user accesses the processor and inputs data through an internet link. In some embodiments, the system is adapted to be connected to the internet such that the output is transmitted to a user via internet.

Isolated MREs and Methods Using the Same

MRE sequences may be incorporated into heterologous mRNAs which do not ordinarily contain such MRE sequences as a means to provide regulation of gene expression. For example, the expression of a gene that includes an added MRE may be regulated using the miRNA to reduce expression levels and eliminating the presence of miRNA to upregulate expression. Such regulation of expression is useful in expression systems where gene expression is detrimental to cell growth and/or cell culture expansion. When down-regulation of expression is desired, expression of genes provided with the MRE can be suppressed by exposing the mRNAs to miRNAs. When increased expression is desired, the presence of miRNA can eliminated or reduced, either by discontinuation of addition miRNA, suppression of expression of genes encoding miRNA or inactivation of miRNA present. Accordingly, the present invention further relates to isolated nucleic acid sequences including RNA and DNA that comprise MRE sequences as well as nucleic acid sequences including RNA and DNA that comprise heterologous MRE sequences as well as methods of using such nucleic acid molecules.

The present invention also refers to isolated nucleic acid molecules that contain one or more MRE free of coding sequence operably linked to regulatory sequences. Such nucleic acid molecules may comprise 2, 3, 4, 5, 6, 7, 8, 9, 10 or more copies of the MRE. Nucleic acid molecules that contain one or more MRE free of coding sequence operably linked to regulatory sequences may be delivered to cells to serve as decoy binding substrate for miRNa in order to upregulate expression of mRNA that contains the MRE. The present invention relates to compositions and vectors for delivering the nucleic acid molecules that contains one or more MRE to the cell expressing the mRNA that contains the MRE.

Novel miRNAs and Methods of Using the Same

The novel miRNAs generated according to the present invention may be synthesized, and in some case tested to confirm their activity. They are useful to downregulate the expression of the gene from which the selected mRNA sequence was derived. According to the invention, miRNAs are delivered to a cell expressing the gene and the amount of protein produced is reduced as the result of the effect of the miRNA on the mRNA that encodes the protein and contains the MRE.

The present invention relates to miRNA compositions that are made by first performing the method to generate them followed by synthesizing them as well as compositions and vectors for delivering the miRNA to the cell expressing the mRNA that contains the MRE.

The microRNAs are useful to down regulate gene expression of mRNA containing the selected mRNA sequence. In some embodiments, the mRNA encodes a protein associated with a disease, condition or disorder and the downregulation of the gene is useful to treat individuals who have the disease, condition or disorder.

EXAMPLES

Example 1

A new paradigm of gene expression regulation has emerged recently with the discovery of microRNAs, an evolutionarily-conserved class of ~22 nucleotide (nt) RNAs. miRNAs control gene expression by base pairing with miRNA recognition elements (MREs) found in their messenger RNA (mRNA) targets. Despite a large number of reported miRNAs their mRNA targets remain elusive. Here we use a combined bioinformatics and experimental approach to identify important rules governing miRNA-MRE recognition that allow prediction of human and mouse miRNA targets. We predict mRNA targets for human and mouse miRNAs and provide a strategy to identify mRNA targets for all known miRNAs.

To search for human miRNA targets we initially employed a bioinformatics approach. We limited our searches to the 3'-UTRs of human mRNAs, extracted from the annotated Reference mRNA Sequences (RefSeq) databaseb (Pruitt et al. 2003), comprising a total of 14,180,360 bases from 16,759 mRNAs. 3'-UTR sequences were used because the experimentally identified MREs for the C. elegans lin-4 and let-7 miRNAs are present in the 3'-UTR of their mRNA targets (Lee et al. 1993; Wightman et al. 1993; Moss et al. 1997; Reinhart et al. 2000). Repetitive elements, such as Alu transposable elements that are embedded in a random fashion in ~5% of all human mRNAs, were filtered out before running the searches (leaving a total of 12,642,810 bases). In this initial search we used ten miRNAs (let-7b, let-7e, miR-141, miR-24, miR-145, miR-23a, miR-15a, miR-16, miR-199b and miR-103) which were arbitrarily chosen except for being conserved between humans and mice. We hypothesized that miRNA:MRE interactions might be guided by two factors. The first might be high affinity interactions, based on binding energies, between a miRNA and its cognate MRE. To address this, we designed an algorithm that allowed us to identify putative miRNA:MRE interactions based on binding energies between two RNAs paired imperfectly. We implemented a modified dynamical programming algorithm that was calculating free energies of both canonical (Watson-Crick) and G-U wobbles dinucleotide base pairs (Tinoco and al 1973) for two RNAs paired in trans. To identify putative MREs, we used a window of 38 nucleotides that "slid" over the mRNA sequence and calculated the minimum binding energy between the miRNAs and sequences in the human 3'-UTR database. Mismatches were allowed and binding energies were calculated for every three consecutive nucleotide pairs. We hypothesized that MREs might be evolutionary conserved and we determined for each human miRNA all the hits that were conserved in the 3'-UTRs of the corresponding mouse ortholog mRNAs. Calculations were performed on a cluster of 128 dual-processor Linux machines.

A second factor that may guide miRNA:MRE (target mRNA) bindings is miRNA-associated protein(s) that impose restraints on the position and sizes of loops and nucleotide bulges between miRNAs and their cognate MREs. miRNP proteins and in particular the Argonaute family of proteins represent excellent candidates for guiding such miRNA:target mRNA interaction (Nelson et al. 2004). In this case there may exist a general set of rules that are applicable to miRNA:MRE bindings and which may be deduced experimentally by testing various miRNA:MRE configurations. Based on this premise we tested a number of putative miRNA:MRE interactions that our initial algorithm had predicted. As a starting point for choosing putative miRNA:MRE interactions for further experiments, we considered miRNA:MRE pairs that had a central bulge or loop of the miRNA or its cognate mRNA. This was based on the experimentally verified C. elegans lin4:lin-14, lin-4:lin-28 and let-7:lin-41 miRNA:target mRNA interactions (Lee et al. 1993) (Wightman et al. 1993) (Moss et al. 1997) (Reinhart et al. 2000). Our experimental strategy consisted of cloning the putative MREs (as single copies) into the 3'-UTR of a reporter construct. Because MREs are necessary and sufficient to confer mi/siRNA-dependent translational repression (Moss et al. 1997) (Reinhart et al. 2000) (Zeng et al. 2002) (Doench et al. 2003), we reasoned that placement of predicted MREs for specific miRNAs in the 3'-UTR of a reporter construct, followed by transfections in cells expressing the miRNAs that recognize the MREs, should lead to a decrease of the reporter protein levels. By visual inspection we collected a number of hypothetical MREs (shown in FIGS. 1, 3, 4; and see below) from the list of conserved human/mouse hits for experimentation. One of the predicted MREs for let-7b was found in the 3'-UTR of both the human and mouse mRNAs that code for the human/mouse homolog of the C. elegans LIN-28 protein, a putative RNA-binding protein (see FIG. 1). This finding is particularly interesting because the lin-28 and let-7 genes function in the same developmental pathway in C. elegans (Moss et al. 1997). The Moss laboratory has shown recently that the expression of LIN-28 protein is developmentally regulated in Drosophila, mouse and Xenopus and in various human and mouse cell lines (Moss and Tang 2003). LIN-28 protein is present early in development and is absent from terminally differentiated cells, a pattern which is similar to the expression pattern of LIN-28 protein in C. elegans (Moss and Tang 2003). Interestingly, HeLa cells do not express LIN-28 protein, a result consistent with the likely repression of lin-28 mRNA translation by let-7b. The Moss laboratory has also identified the same MRE for let-7b in the 3'-UTR of the human and mouse lin-28 mRNA (Moss and Tang 2003).

We decided to investigate more thoroughly this putative interaction by extensive mutagenesis, as detailed below.

We cloned the predicted lin-28 MRE into the 3'-UTR of a *Renilla* Luciferase (RL) reporter construct. As a positive control, we generated two RL constructs each bearing in the 3'-UTR one of the two reported MREs for let-7, derived from the *C. elegans* lin-41 mRNA, an experimentally verified let-7 target (Reinhart et al. 2000). As a negative control, the sequence of the lin-28 MRE was scrambled and placed in the 3'-UTR of RL. We cotransfected the RL-MRE bearing constructs along with a plasmid encoding Firefly Luciferase (FL) in two different cells lines: HeLa cells (a human epithelial cell line) and MN-1 cells (a mouse motor neuronal cell line). These cell lines normally express let-7 paralogs, which are conserved between humans and mice (Lagos-Quintana et al. 2001; Dostie et al. 2003)). 18 hours after transfection we quantitated the levels of normalized RL/FL using standard luminometric assays. As shown in FIG. 1, we consistently observe ~5-fold reduction in the protein levels of RL bearing the lin-28 MRE versus RL bearing the scrambled MRE (negative control), an effect which is stronger than that of the two positive control MREs derived from lin-41 (LIN-41a and LIN-41b, FIG. 1). Similar results were obtained with both cell lines when the luminometric assays were performed 16, 24 or 48 hours after transfections. These results confirm the validity of the predicted lin-28 MRE. We have further demonstrated that in a human neuronal cell line, a Gemin3-Gemin4-Argonaute-let-7b containing miRNP associates physically with endogenous lin-28 mRNA in polyribosomes only (Nelson et al. 2004), suggesting that there is an in vivo, interaction between let-7b and lin-28 mRNA. Because other human let-7 paralogs show extensive homology to let-7b (Lagos-Quintana et al. 2001), they are also likely to recognize the lin-28 mRNA. Collectively, these findings strongly suggest that human lin-28 mRNA constitutes a target for let-7b and its paralogs.

Figure 1B:
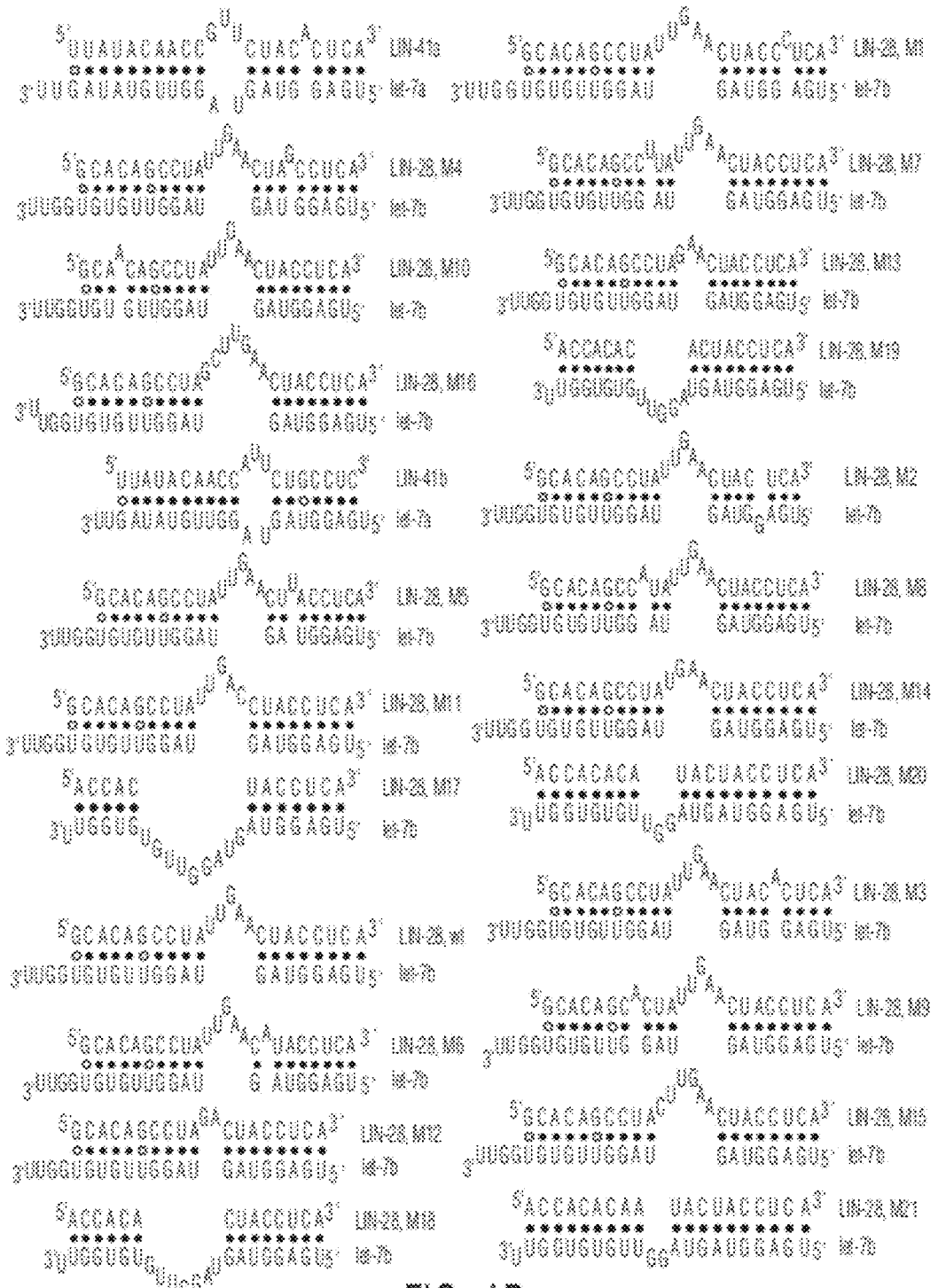
Figure 1C:
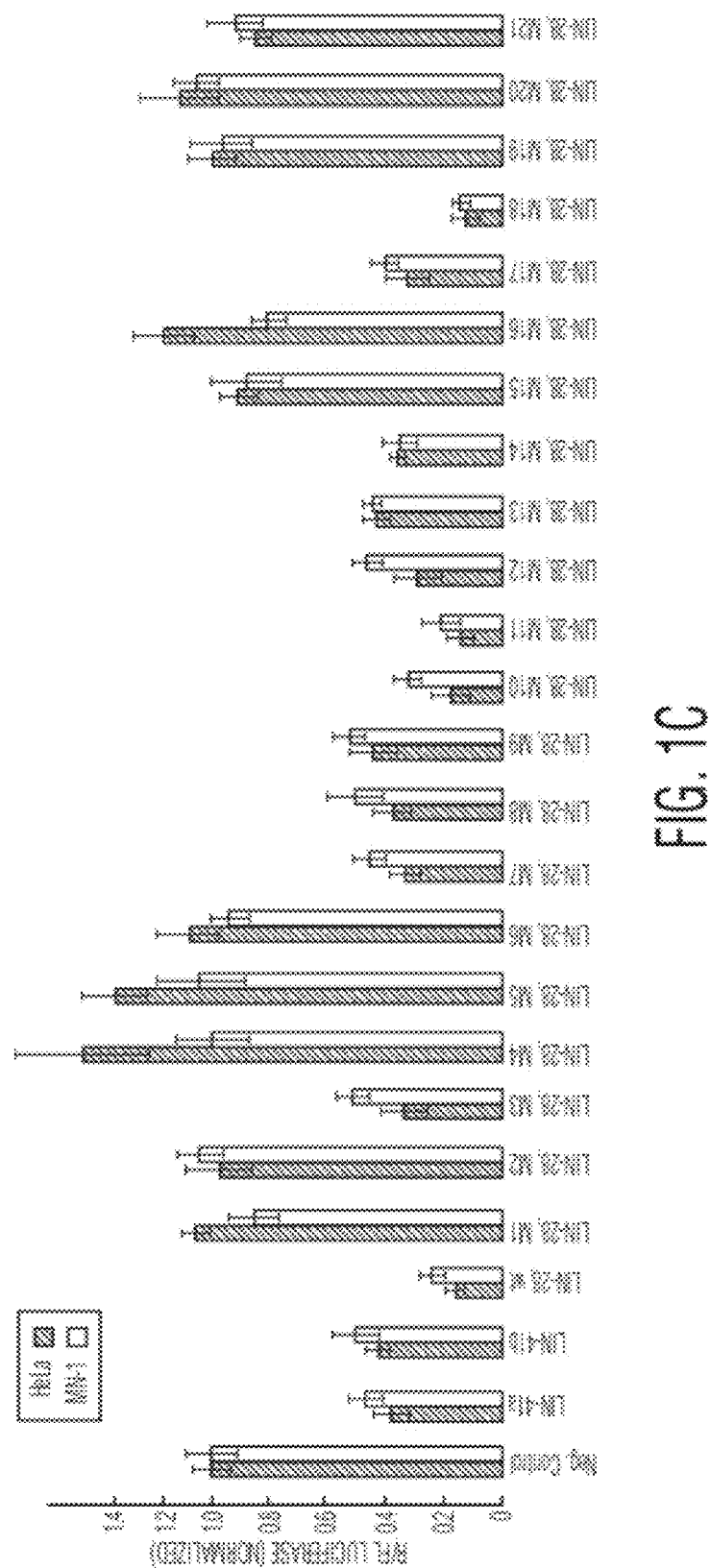
Figure 1D:
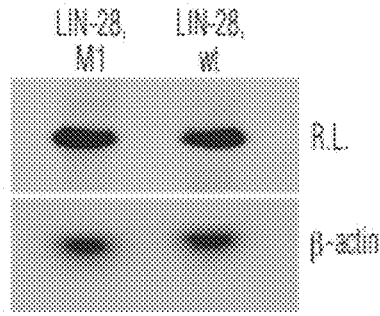

We next wished to investigate further the rules governing miRNA:MRE interactions by generating a series of mutant lin-28 MREs with varying potentials to base pair with the human/mouse let-7b miRNA (FIG. 1B). These MREs were tested as described above, in HeLa and MN-1 cells. As shown in FIG. 1C, with the exception of LIN-28-M3 MRE, single nucleotide bulges between let-7b and the lin-28 mutant MREs that map towards the 5'-end of let-7b, abolish repression of RL expression (mutants LIN-28-M1, -M2, -M4, -M5 and -M6). The single nucleotide bulge of LIN28-M3 MRE is symmetrically placed between the beginning of the loop and the beginning of base pairing between the 5'-most let-7b nucleotide with LIN-28-M3 (i.e. this single nucleotide bulge is surrounded by an equal number of base-paired nucleotides). A similarly placed single nucleotide bulge is found between let-7a and LIN-41a (one of the two LIN-41 MREs, present in the 3'-UTR of the *C. elegans* lin-41 mRNA; FIG. 1). The activities of both of these MREs are similar (compare LIN-41a to LIN-28, M3 in FIG. 1C). These results show that near perfect complementarity between the first ~9 nucleotides (from the 5'-end) of a miRNA and its cognate MRE is required for miRNA function; and the 5' most nucleotide of miRNAs is not required to base pair with MREs (see bindings between LIN-41a or LIN-41b MREs with let-7a in FIG. 1B). We refer to this region of the miRNA as the proximal region.

Analysis of published work on si/miRNAs, provides further support for this claim. In the experimentally verified MREs for lin-4 and let-7, there is perfect base pairing between the MREs and the first seven or eight (starting from the 5'-end of the miRNA) nucleotides of each miRNA with none or only a single symmetrically placed nucleotide bulge; and the 5' most nucleotide of lin-4 and let-7 may or may not base pair with MREs (Moss et al. 1997; Reinhart et al. 2000). Two loss-of-function mutants of lin-4 and let-7 miRNAs, identified in genetic screens, are caused by single-point mutations mapping in the first 6 nucleotides in both miRNAs and are predicted to disrupt base pairing in the proximal region (Lee et al. 1993; Moss et al. 1997; Reinhart et al. 2000). In the experimentally verified target for bantam miRNA there is perfect complementarity between the MREs and the proximal region of each miRNA (Brennecke et al. 2003). The 5'-end of siRNAs sets the "ruler" for target RNA cleavage, implying that recognition of the 5'-end of siRNAs is essential for their function (Elbashir et al. 2001). A genetic, single-point mutation, present in the MRE of the Arabidopsis PHAVOLUTA (PHV) mRNA, disrupts base pairing with the fifth nucleotide of its cognate miR-165/166 miRNA and reduces dramatically the miR-165/166-mediated cleavage of the mutant phv mRNA (Tang et al. 2003). Single point mutations mapping in the first 7 nucleotides of an siRNA reduce siRNA activity, whereas point mutations mapping towards the 3'-end of the siRNA have no or much smaller effects (Amarzguioui et al. 2003). A subset of *Drosophila* miRNAs show perfect complementarity between their proximal region and 3'-UTR elements that are known to mediate negative posttranscriptional regulation, in flies (Lai 2002). Computational prediction and experimental verification of 6 *Drosophila* miRNA targets, using reporter constructs, shows that perfect complementarity of the proximal miRNA region is required for repression of reporter expression (Stark et al. 2003) Computational prediction of mammalian miRNA targets and experimental verification of 11 human miRNA targets, shows that complementarity between nucleotides 2 to 8 (proximal region) of mammalian miRNAs and their targets, is critical for target recognition by miRNAs (Lewis et al. 2003). Translational repression of miRNA targets bearing multiple MREs, is largely determined by perfect complementarity between the MREs and the proximal miRNA region (Doench and Sharp 2004).

In contrast to the strict requirements for base-pairing at the proximal region, nucleotide bulges between lin-28 mutant MREs and the 3'-end of let-7b, (a region that we refer to as the distal region), are tolerated and decrease by ~2-fold the activities of the mutant lin-28 MREs (FIG. 1; LIN-28-M7, -M8 and -M9). The activity of LIN-28-M10, which bears a single nucleotide mismatch away from the central bulge and close to the 3'-end of let-7b is essentially the same with that of the wild-type lin-28 MRE. We next determined the requirements for the size and position of the central bulges between let-7b and mutant lin-28 MREs. The optimal length of the central bulge found in the wild-type lin-28 MRE is 5 nucleotides. As shown in FIG. 1, lin-28 mutant MREs with single, symmetrically placed central bulges varying in size from 2 to 4 nucleotides were still active (LIN-28-M12 to -M14), while a single nucleotide substitution of the lin-28 central bulge had the same activity as the wild-type lin-28 MRE (LIN-28-M11). However, lin-28 mutant MREs with central bulges longer than 5 nucleotides were unable to repress the *Renilla* luciferase activity (LIN-28-M15, -M16). Finally, mutant lin-28 MREs were designed that allowed for a single let-7b central bulge of varying sizes. As shown in FIG. 1, MREs with a 9 nt or 7 nt let-7b central bulge were active (LIN-28-M17, -M18) but MREs with a let-7b central bulge of less than 5 nucleotides were inactive (LIN-28-M19 to -M21). In fact, the activity of LIN-28-M18 MRE is identical to the wild-type LIN-28 MRE, and resembles the binding characteristics between the *C. elegans* lin-4 miRNA and its lin-28 mRNA target (Moss et al. 1997) (see also FIG. 6C). To verify that the reduction of the Renilla luciferase activity was due to let-7b-mediated translational repression, we performed Northern blots on total RNA isolated from HeLa cells that had been transfected with LIN-28-wt or LIN-28-M1 constructs. As shown in FIG. 1D, the mRNA levels between these two constructs were unchanged, ruling out the possibility that the observed reduction of the *Renilla* luciferase activity in the construct bearing the wild-type LIN-28 MRE (LIN-28-wt) was secondary to destabilization of its mRNA.

These experiments demonstrate that there are discernible rules that govern miRNA:target mRNA interactions, which may be generally applicable. We note that the repressing properties of a miRNA may depend on the way it interacts with its mRNA target. A miRNA:MRE (target mRNA) interaction with a central bulge of optimal length (LIN-28, wt and LIN-28, M18; FIG. 1) is more potent than two small opposing loops (LIN-41a or LIN-41b; FIG. 1). This finding may explain the requirement, for optimal repression, of two MREs for let-7 in the 3'-UTR of the *C. elegans* lin-41 mRNA (Reinhart et al. 2000). On the other hand, a single MRE for lin-4 in the 3'-UTR of the *C. elegans* lin-28 mRNA suffices because it contains a single, 6 nucleotides central bulge (Moss et al. 1997). The degree of miRNA-mediated translational repression may ultimately depend on additional factors such as the miRNA and target mRNA concentrations, the presence of multiple MREs on target mRNAs, the accessibility of MREs and other cis elements. Indeed, in vivo repression of the *C. elegans* lin-41 mRNA expression by let-7 requires, in addition to the two MREs recognized by let-7, a stretch of 27 nucleotides between the two MREs. This finding suggests that the context of MREs is also important for miRNA-mediated regulation (Vella et al. 2004).

The finding of a let-7b MRE in the 3'-UTR of the human/mouse lin-28 mRNA and the fact that endogenous human lin-28 mRNA associates with a let-7b-containing miRNP in polyribosomes (Nelson et al. 2004) along with the regulation of LIN-28 protein expression as reported by the Moss lab (Moss and Tang 2003) strongly suggest that human let-7b and lin-28 are part of the same pathway, which may be functionally related to the *C. elegans* heterochronic gene pathway. The *C. elegans* lin-28 mRNA is predominantly regulated by lin-4 (Moss et al. 1997). Although a direct role for let-7 in the regulation of *C. elegans* lin-28 mRNA has not been shown, lin-28 is also regulated by a lin-4 independent pathway (Seggerson et al. 2002). There are four let-7 paralogs in *C. elegans* and it is possible that one of them regulates lin-28.

Figure 2A:
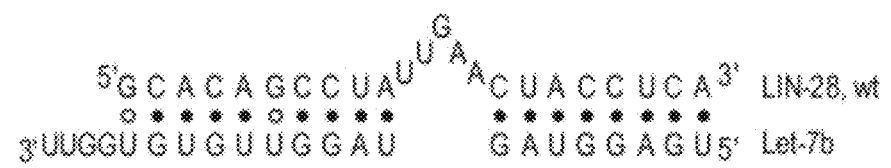
FIGS. 2A, 2B, and 2C describe restoration of miRNA-mediated translational repression of LIN-28 mutant MREs by synthetic let-7b siRNAs that carry compensatory mutations.
Figure 2A:
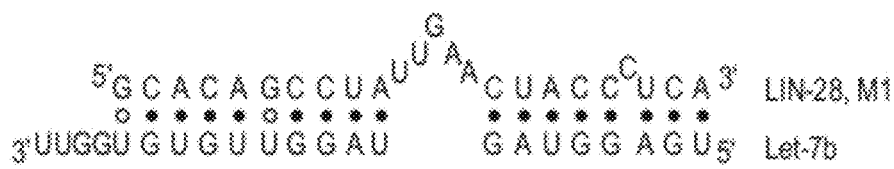
Figure 2A:
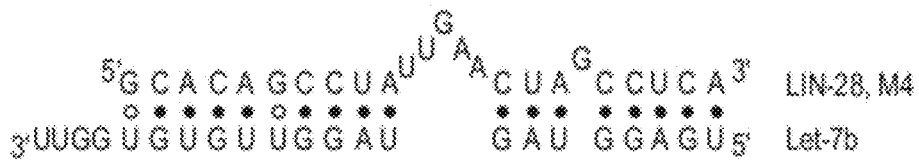
Figure 2A:
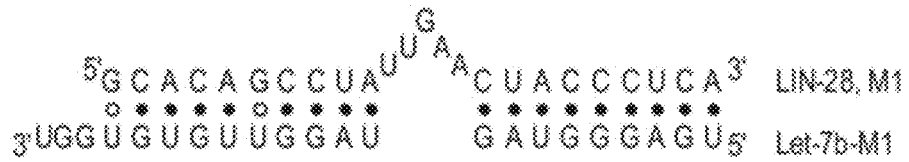
Figure 2A:
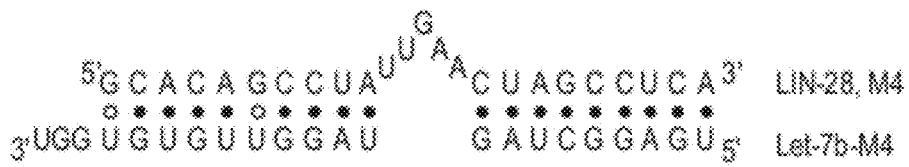
Figure 2B:
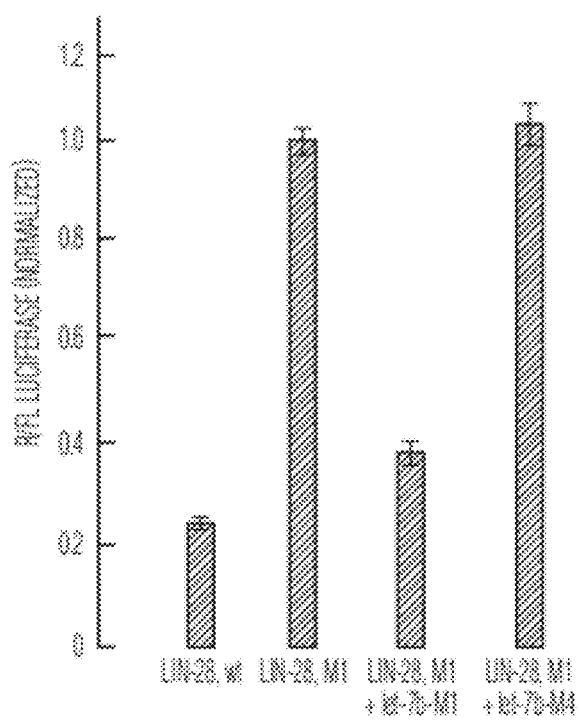
Figure 2C:
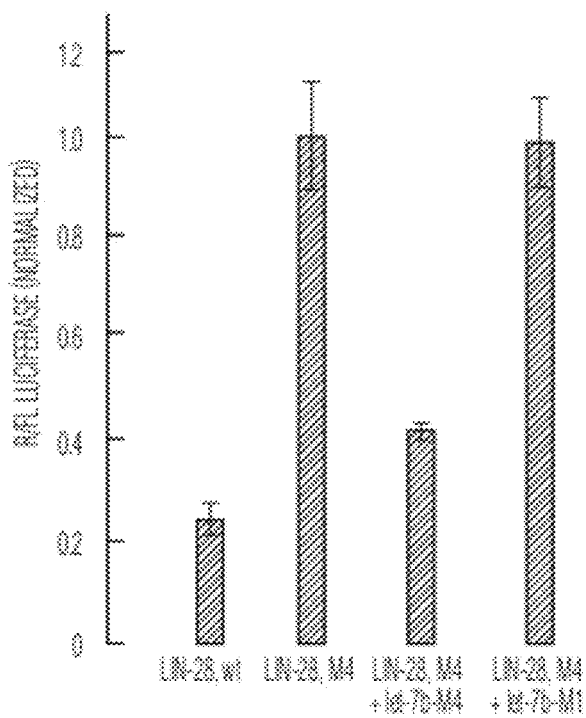

To test further the validity of our findings we made synthetic let-7b siRNAs (let-7b-M1 and let-7b-M4) carrying point mutations designed to compensate the point mutations found in two of the lin-28 MRE mutants (LIN-28-M1 and LIN-28-M4 respectively; see FIG. 2A). Sharp and colleagues have demonstrated the feasibility of transfecting siRNAs that function as miRNAs (Doench et al. 2003). LIN-28 constructs (FIG. 2) were transfected with or without these siRNAs and the *Renilla* luciferase activity was measured 18 hours after transfection. As shown in FIG. 2B, cotransfection of the LIN-28-M1 construct with let-7b-M1 siRNA repressed the levels of luciferase, whereas cotransfection of LIN-28-M1 with let-7b-M4 siRNA had no effect. Similarly, cotransfection of the LIN-28-M4 construct with let-7b-M4 siRNA repressed the levels of luciferase, whereas cotransfection of LIN-28-M4 with let-7b-M1 siRNA had no effect (FIG. 2C). The suppression of the luciferase activity with siRNAs carrying compensatory mutations is significant, specific and reproducible, but it is not as pronounced as the one seen with the endogenous let-7b miRNA targeting the wild-type lin-28 MRE. This may reflect inefficient incorporation of exogenous siRNAs in miRNPs/RISCs. These siRNA duplexes were designed prior to the reports, by Khvorova and colleagues (Khvorova et al. 2003) and Zamore and colleagues (Schwarz et al. 2003), describing the functional assymetry of siRNA duplexes and siRNA-like duplexes (derived from Dicer processing of pre-miRNAs). These studies show that there is preferential incorporation in RISCs of siRNAs and miRNAs whose 5'-end is more loosely paired with its antisense (Khvorova et al. 2003) (Schwarz et al. 2003). We note that, for both siRNA duplexes used in the experiment of FIG. 2, the 5'-end of the antisense siRNA strand (which is predicted to base-pair with the MRE) starts with a Uridine and the 5'-end of the sense siRNA strand starts with a Cytosine. In that regard, our siRNA duplexes conform to the design rules that maximize incorporation of siRNAs in RISCs. However, for the siRNA-like duplexes that are derived from pre-miRNAs (including pre-let-7b), an unpaired 5'-end of the miRNA is best suited for efficient incorporation in miRNPs/RISCs (Khvorova et al. 2003) (Schwarz et al. 2003). Our siRNA duplexes might have been more efficient in repressing the expression of the reporter constructs had we used unpaired 5'-ends of the antisense strands. In summary, these experiments demonstrate the validity of the miRNA binding rules and the exquisite specificity of the miRNA:MRE interaction.

Figure 3A:
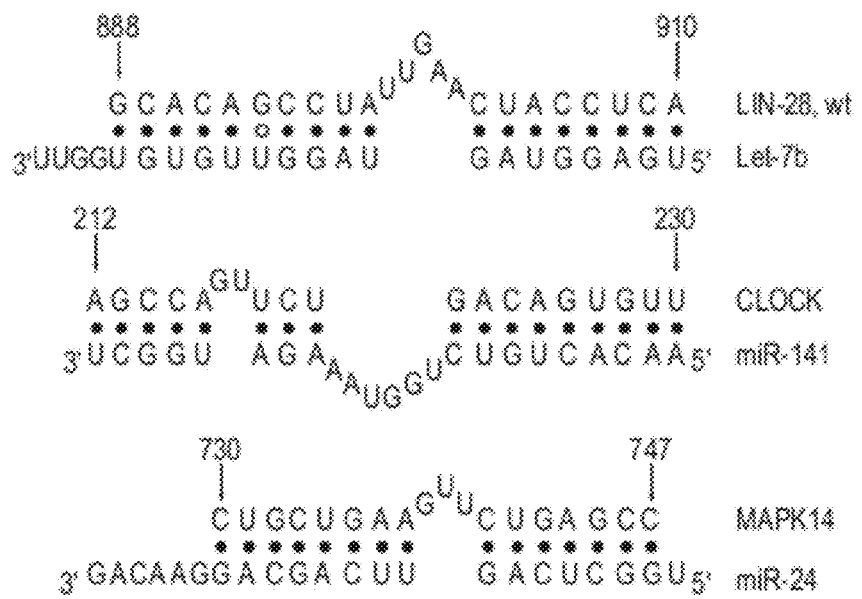
FIGS. 3A and 3B show predicted miRNA targets.
Figure 3B:
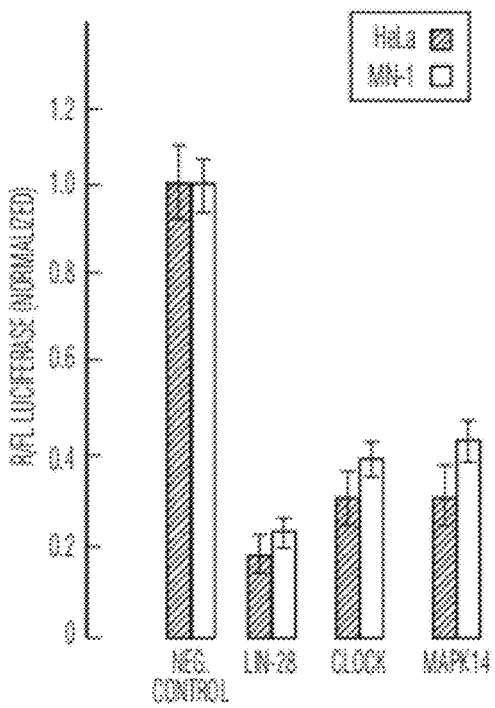
Figure 4:
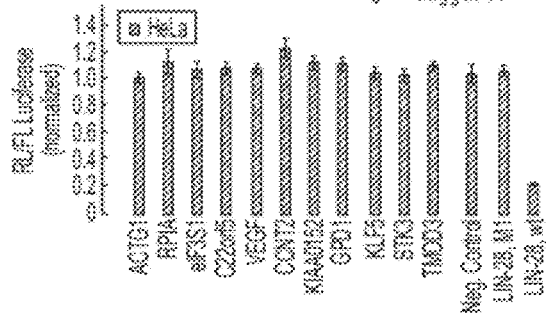
FIG. 4 shows miRNA:MRE configurations that do not repress translation. HeLa cells were cotransfected with Renilla Luciferase (RL) constructs bearing the indicated MREs in the 3'-UTR, along with Firefly Luciferase (FL). Results shown are average values (with standard deviations) of normalized RL/FL activities obtained from three separate experiments. The sequence identified as Let-7b-M1 is SEQ ID NO:27. The sequence identified as Actin Top String is SEQ ID NO:33. The sequence identified as Actin Bottom String is SEQ ID NO:34. The sequence identified as Ribose 5-phosphate isomerase A Top String is SEQ ID NO:35. The sequence identified as Ribose 5-phosphate isomerase A Bottom String is SEQ ID NO:36. The sequence identified as eIF3S1 Top String is SEQ ID NO:37. The sequence identified as eIF3S1 Bottom String is SEQ ID NO:38. The sequence identified as C22orf5 Top String is SEQ ID NO:39. The sequence identified as C22orf5 Bottom String is SEQ ID NO:40. The sequence identified as VEGF Top String is SEQ ID NO:41. The sequence identified as VEGF Bottom String is SEQ ID NO:42. The sequence identified as Cyclin T2 Top String s SEQ ID NO:43. The sequence identified as Cyclin T2 Bottom String is SEQ ID NO:44. The sequence identified as KIAA0152 Top String is SEQ ID NO:45. The sequence identified as KIAA0152 is SEQ ID NO:46. The sequence identified as GPD1 Top String is SEQ ID NO:47. The sequence identified as GPD1 Bottom String is SEQ ID NO:48. The sequence identified as KLF5 Top String is SEQ ID NO:49. The sequence identified as KLF5 Bottom String is SEQ ID NO:50. The sequence identified as STE-20 Top String is SEQ ID NO:51. The sequence identified as STE20 Bottom String is SEQ ID NO:52. The sequence identified as TMOD3 Top String is SEQ ID NO:53. The sequence identified as TMOD3 Bottom String is SEQ ID NO:54.

In parallel, we experimentally tested all hypothetical miRNA:MRE configurations shown in FIGS. 3 and 4. The miRNAs (let-7b, let-7e, miR-141, miR-24, miR-145, miR-23a, miR-15a, miR-16, miR-199b and miR-103) for these putative targets are present in both HeLa and MN-1 cells (Lagos-Quintana et al. 2001; Lagos-Quintana et al. 2002; Mourelatos et al. 2002; Dostie et al. 2003). miR-141 was originally cloned from mouse (Lagos-Quintana et al. 2002). Human miR-141, containing two additional terminal nucleotides, has also been cloned from human colonic mucosa (Michael et al. 2003) (originally deposited in the Genbank database as accession AJ535825). We have cloned miR-141 from HeLa and MN-1 cells and confirmed the presence of the two additional nucleotides as shown in FIG. 3A. Whether the longer or shorter miR-141 is more prevalent in cells is unknown. These miRNA:MRE configurations were chosen based on their general resemblance to the experimentally verified *C. elegans* miRNA:target mRNA interactions, as described above, and prior to the completion of the mutational analysis presented in FIG. 1. All of these putative MREs were also conserved in the mouse. Only two (in addition to lin-28) of these putative MREs suppressed the expression of luciferase (FIG. 3), whereas II hypothetical MREs failed to do so (FIG. 4). These findings are entirely consistent with the results of our mutational analysis of the let-7b:lin-28 interaction and further demonstrate the high specificity of the miRNA:MRE bindings. For example, the main difference between the binding characteristics between miR-141 and its true MRE found in the Clock mRNA (which suppresses the levels of the reporter; FIG. 3B) versus mir-141 and STK3 (which does not suppress the levels of the reporter; FIG. 4) is in the number of nucleotides of the miRNA central bulge. In the second case (which is inactive) that bulge is 5 nucleotides. This result is expected based on the results of our mutational analysis because a lin-28 mutant that has the same configuration (LIN-28, M19; FIG. 1) with that of miR-141:STK3, is unable to repress the expression of the reporter. Based on these findings and the results of the mutational analysis a general set of miRNA binding rules may be formulated and is shown in FIG. 5A.

Figure 5B:
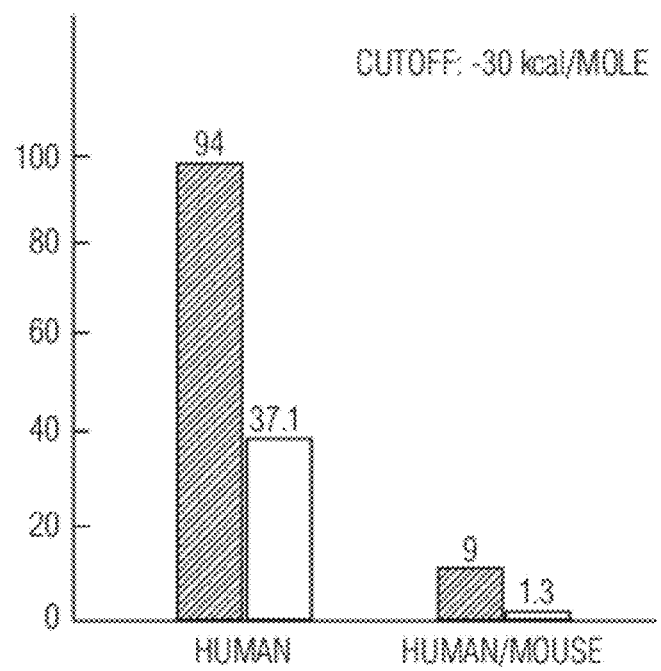
Figure 5C:
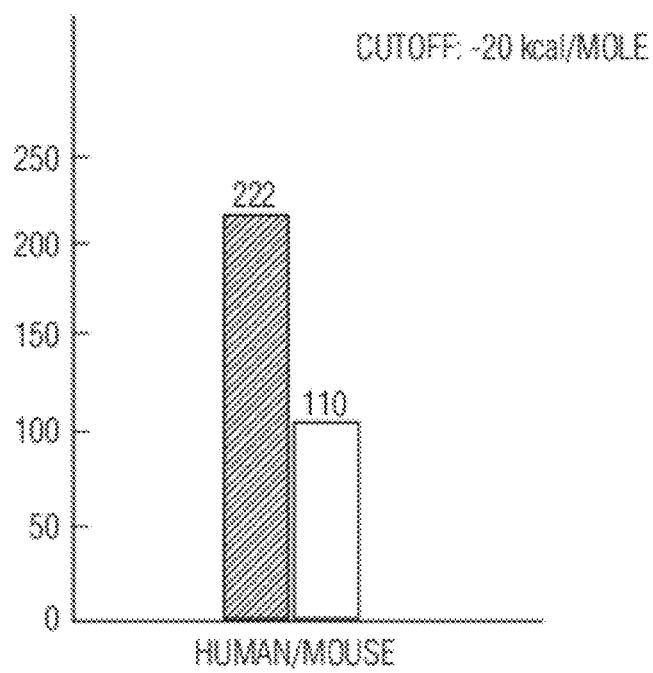

We subsequently combined our initial algorithm with an "MRE filter" to create the computational program which predicted 94 human MREs for the 10 miRNAs (using a cutoff of −30 kcal/mole; FIG. 5B). Nine of the predicted human MREs are also conserved in the 3'-UTRs of the corresponding mouse ortholog mRNAs. To evaluate the statistical significance of our computational algorithm, we created a cohort of "negative control" sequences by randomly shuffling the sequence of each of the ten real miRNAs, ten times. All of the ten randomized sequences for each miRNA (amounting to a total of 100 randomized sequences) were used for the computational searches. 371 "MREs" were predicted for these 100 randomized sequences, 13 of which were also conserved in the mouse. Normalizing the numbers for the 10 miRNAs, the total number of predicted "MREs" for the randomized RNA sequences was 37.1 (human) or 1.3 (conserved human/mouse; FIG. 5B). Thus, the average number of human MREs predicted for each real miRNA is 9.4 versus 3.7 for each shuffled. It is important to note that this significant difference between the number of predicted MREs for the real miRNAs versus the shuffled sequences, is seen only when the miRNA binding rules are implemented in the computational algorithm. Using the −30 Kcal/mole energy cut-off as the only criterion for MRE prediction, revealed an average number of 5,094 predicted human MREs for each miRNA versus 4,974 for each shuffled. No differences were detected when we determined the numbers of those MREs that were conserved in the mouse: 168 on average for each real miRNAs versus 158 for each shuffled. We also determined which of the human MREs for the queried miRNAs were conserved in other species.

During this initial analysis, we observed that many putative human MRE sequences were not detected in the 3'-UTR of homologous mRNAs from mouse because of the small mouse 3'-UTR database that we used. Conservation of predicted MREs provides a strong indication for the biological importance of these sites. During the next phase of our analysis, we used 84 additional miRNAs (for a total of 94 miRNAs) that are non-redundant and perfectly conserved between humans and mice. These include the 79 miRNAs that Lewis et al. used in their study (Lewis et al. 2003). We also created a program that generates shuffled miRNA controls that have the same compositional properties with the authentic miRNAs, and take into account the nucleotide composition biases of mammalian 3'-UTRs (Lewis et al. 2003) (Nussinov 1981). We generated a new set of 3'-UTR databases by extracting the conserved human and mouse 3'-UTRs from orthologous genes using EnsMart (Kasprzyk et al. 2004). This new approach increased significantly the number of orthologous genes with conserved 3'-UTRs (derived from 13,272 human transcripts; versus 4035 in our previous database). Finally, computationally based upon complementarity, we predicted conserved human/mouse targets using the new datasets along with the new control (shuffled) sequences and using an energy threshold cutoff of −20 kcal/mole. We predicted 5,031 human targets for the 94 miRNAs; 222 of these targets are also conserved in the mouse. The ratio of conserved:all hits for the 94 authentic miRNAs is 1:22.6. For the control sequences (376 shuffled controls; 4 for each miRNA) we obtained 15620 human hits, 441 of which were conserved in the mouse. The ratio of conserved:all hits for the 376 shuffled control sequences is 1:35.4. Normalizing the numbers for the 94 miRNAs, the total number of conserved hits for the shuffled controls is 110. The ratio of the conserved human/mouse targets for the authentic versus the shuffled miRNAs is thus 2:1, similar to the value obtained by Lewis et al. (Lewis et al. 2003) for the conserved human/mouse hits. We note that of the 94 miRNAs, conserved MREs were found for 73 miRNAs, suggesting that miRNA targets containing single MREs are less prevalent than targets containing multiple MREs and that some miRNAs may recognize only targets with multiple MREs. However, it is also very likely that additional rules exist for miRNAs that recognize single MREs. Thus, our current analysis may underestimate the number of miRNA targets bearing single MREs.

Figure 6A:
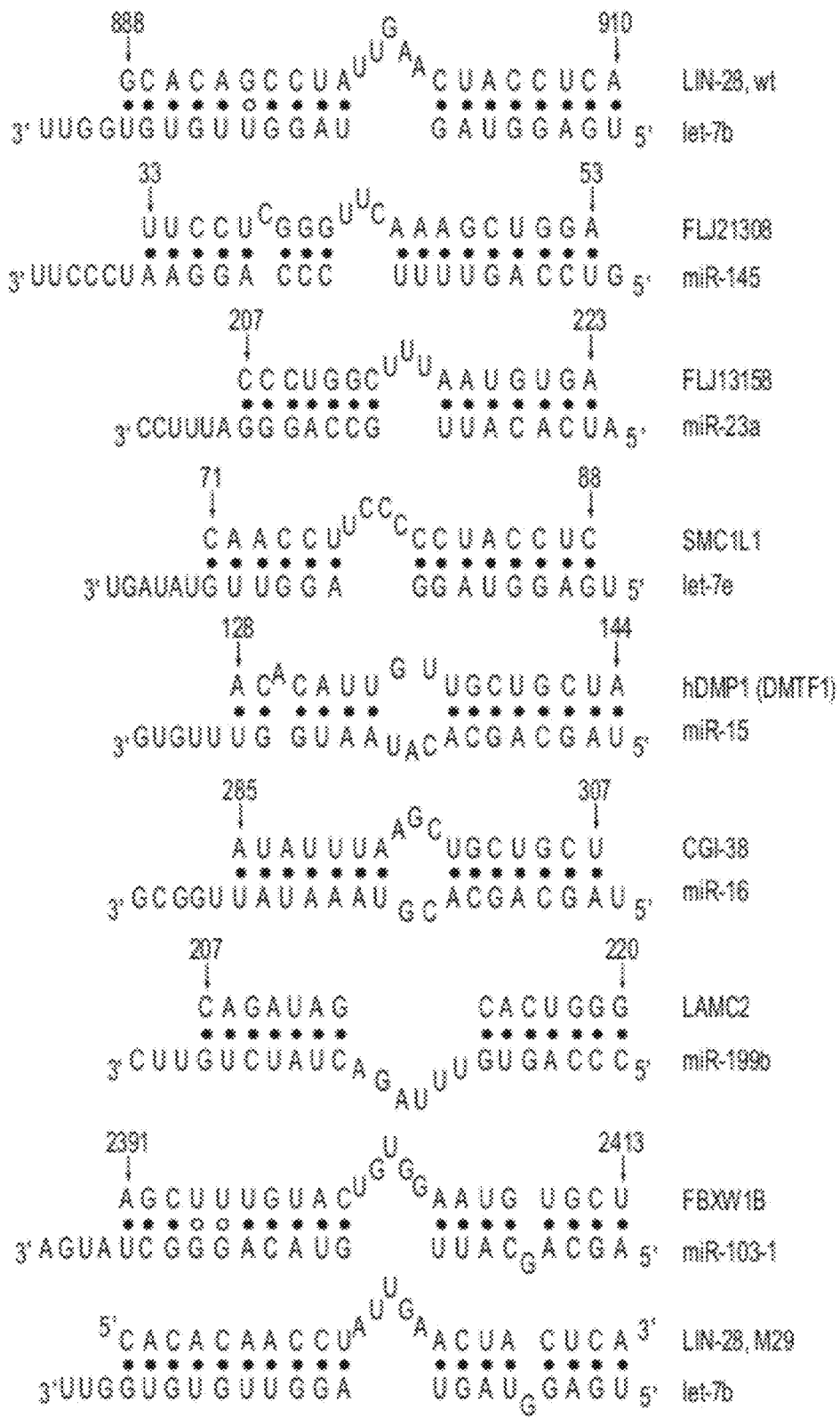
FIGS. 6A and 6B show additional, predicted miRNA targets. The LIN-28, M29:let-7b was designed to mimic the binding characteristics of FBXWIB:miR-103 (which allows for a symmetrically placed single nucleotide bulge of the miRNA at the proximal region of the miRNA:MRE binding).
Figure 6B:
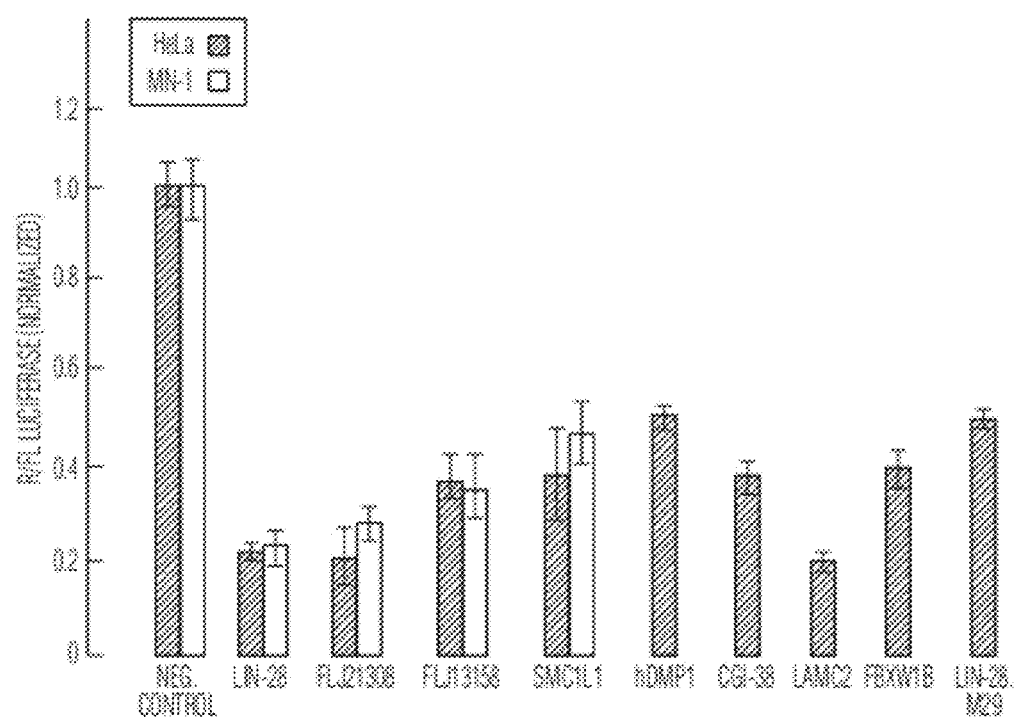

To further validate the results of the final computational analysis, we experimentally verified MREs that were predicted based on the miRNA binding rules. We chose to verify one predicted MRE for each of the miRNAs that we had previously tested with "MREs" that did not abide by the miRNA binding rules (and thus did not suppress the levels of the luciferase reporter as shown in FIG. 4). Seven MREs that abided by the miRNA binding rules were selected, two of which (FLJ13158 and SMCL1) are found in the 3'-UTR of human mRNAs only, whereas the remainder are also conserved in the 3'-UTR of their mouse orthologs. As shown in FIG. 6 (A & B), all of these MREs suppressed the levels of the luciferase reporter. These findings provide further evidence for the validity of the miRNA binding rules. Among the mRNAs that may be regulated by miRNAs are the Clock transcription factor, which is critical for circadian rhythms and the Mitogen-Activated Protein Kinase 14 (MAPK14, also known as p38α kinase). MAPK14 has pleiotropic cellular effects; it is a key regulator of stress-induced signaling, cell proliferation and apoptosis and development (see OMIM entry 600289). Targets for miR-15a and miR-16 are particularly interesting because these miRNAs may play a role in the pathogenesis of B-cell chronic lymphocytic leukemia (Calin et al. 2002). miR-15a may regulate the known tumor suppressor gene Cyclin D-binding Myb-like protein (DMPI/DMTFI) while miR-16 may regulate, among other genes, the mRNA coding for a −25 Kda protein (CGI-38) which is conserved in worms, flies, rodents and humans. A MRE for miR-145 is found in the 3'-UTR of both human and mouse mRNAs coding for a hypothetical 501 amino-acid protein termed FLJ21308 in humans and DI3Ertd275e in mouse. FLJ21308 contains a putative poly (ADP-ribose) polymerase catalytic domain, suggesting that it may function in DNA damage control. For let-7e and miR-23 miRNAs, MREs were found in the 3'-UTR of human mRNAs coding for the structural maintenance of chromosomes 1-like I protein (SMCILI) and a 324 amino-acid hypothetical protein termed FLJ13158, respectively. SMCL1 functions in sister chromatid cohesion during mitosis (see OMIM entries 606462 and 300040). The FLJ13158 protein contains a 120 amino-acid domain of unknown function (termed the DUF738 domain), which is highly conserved in worm, fly, rodent and human proteins. It is possible that some miRNAs may regulate mRNA targets in humans that are not regulated by the same miRNAs in mouse or other species. The length of 3'-UTRs increases with evolutionary age and organism complexity (with human mRNAs having the longest 3'-UTRs (Pesole et al. 2002) (Mazumder et al. 2003). The longer 3'-UTRs may provide more regulatory elements that may contribute to a more complex posttranscriptional regulation of mRNAs in humans. However, predicted MREs that are not conserved in other species should be approached cautiously.

Ultimately, the contribution of a given miRNA in the regulation of its mRNA target may depend on multiple factors including the presence of other cis regulatory elements in the 3'-UTR of the mRNA target.

Figure 6C:
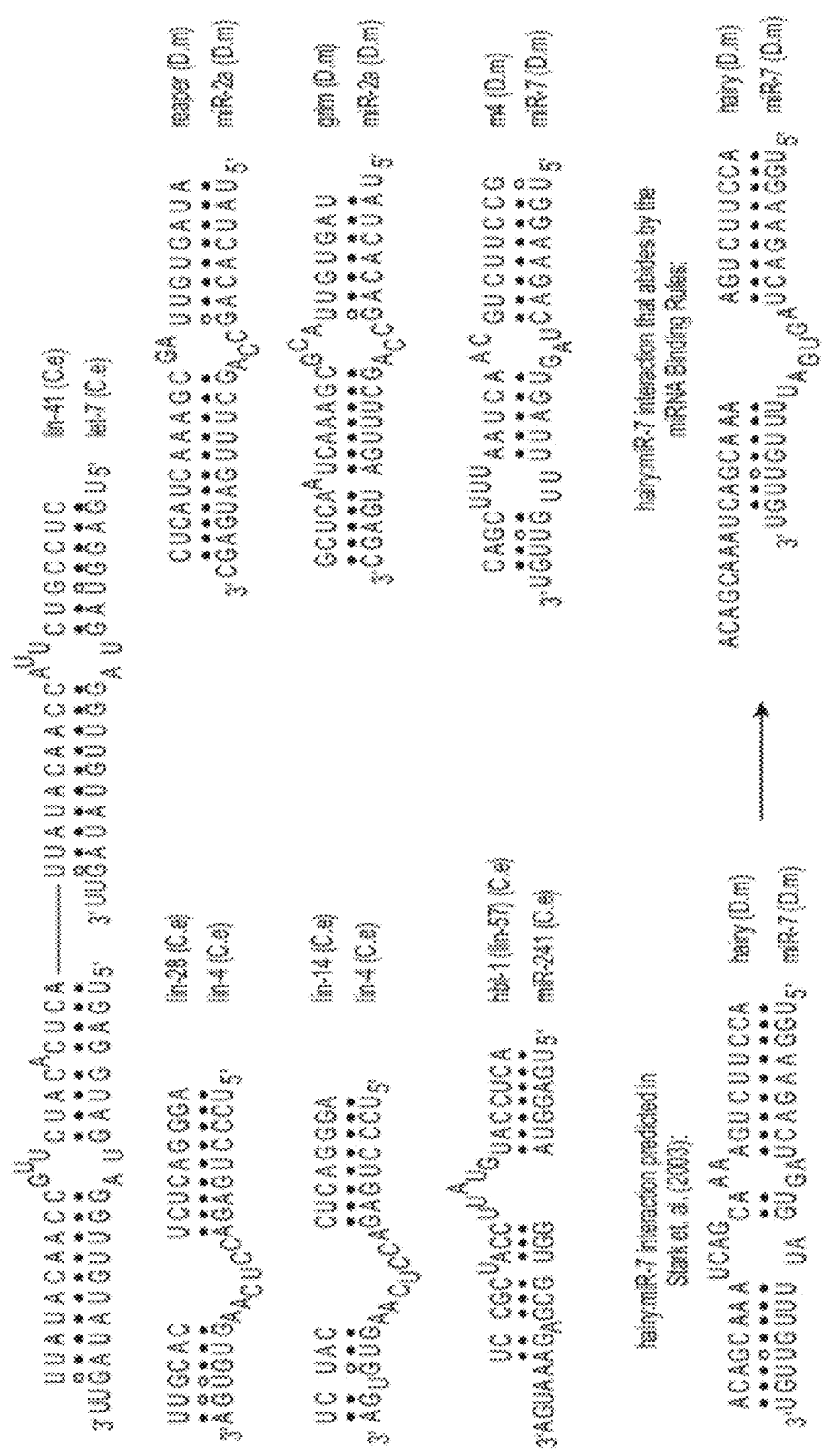
FIG. 6C shows miRNA:MRE (target mRNA) interactions from *C. elegans* (C.e) or *Drosophila melanogaster* (D.m) targets that abide by the miRNA Binding Rules. The sequence identified as Lin-41 (C.e.) (on the 5 prime end) is SEQ ID NO:70. The sequence identified as Lin-41 (C.e.) (on the 3 prime end) is SEQ ID NO:72. The sequence identified as let-7 (C.e.) is SEQ ID NO:71. The sequence identified as lin-28 (C.e.) is SEQ ID NO:73. The sequence identified as lin-4 (C.e.) is SEQ ID NO:74. The sequence identified as lin-14 (C.e.) is SEQ ID NO:75. The sequence identified as hb-1 (C.e.) is SEQ ID NO:76. The sequence identified as miR-241 (C.e.) is SEQ ID NO:77. The sequence identified as hairy (D.m.) is SEQ ID NO:78. The sequence identified as miR-7 (D.m.) is SEQ ID NO:79. The sequence identified as reaper (D.m.) is SEQ ID NO:80. The sequence identified as miR-2a (D.m.) is SEQ ID NO:81. The sequence identified as grim (D.m.) is SEQ ID NO:82 The sequence identified as m4 (D.m.) is SEQ ID NO:83.

We next wished to determine which of the previously identified (and experimentally verified) worm and fly miRNA targets (Lee et al. 1993) (Wightman et al. 1993) (Moss et al. 1997) (Reinhart et al. 2000) (Brennecke et al. 2003) (Lin SY 2003) (Abrahante J E 2003) (Stark et al. 2003) contained MREs that abided by the miRNA binding rules. All three prototypical C. elegans miRNA targets (lin-14, lin-28 and lin-41 mRNAs) (Lee et al. 1993) (Wightman et al. 1993) (Moss et al. 1997) (Reinhart et al. 2000) contain miRNA: MRE interactions that abide by the miRNA binding rules (FIG. 6C). The *C. elegans* ortholog of the *Drosophila* hunchback gene (hbl-1, also known as lin-57) has recently been identified as a heterochronic gene that may be regulated by miRNAs. Multiple potential sites (putative MREs) that may be recognized by various miRNAs have been proposed (Abrahante J E 2003; Lin S Y 2003). We searched for putative hbl-1 MREs with our computational algorithm and found that an MRE for the *C. elegans* miR-241 is found in the 3'-UTR of hbl-1 (FIG. 6C). This MRE is also conserved in the 3'-UTR of the *C. briggsae* hbl-1. Interestingly, miR-241 is a paralog of let-7 and has an identical temporal expression pattern with let-7 (Lim et al. 2003). It is likely that miR-241, like let-7, controls heterochronic genes. Our algorithm predicts that hbl-1 is likely regulated by miR-241.

Recently, putative miRNA targets for 75 *Drosophila* miRNAs have been proposed (Stark et al. 2003). The computational algorithm used in that study was based on binding energies and required complete complementarity between the first eight nucleotides of the miRNA with its putative target (Stark et al. 2003). The database used for the searches consisted of the conserved *D. melanogaster* and *D. pseudoobscura* 3'-UTRs and hits were scored based on the binding energy of the predicted miRNA:MRE interaction, the presence of multiple miRNA sites in the 3'-UTR of putative mRNA targets and the conservation of the sites in a third genome (i.e. *Anopheles gambiae*) (Stark et al. 2003). The presence of multiple MREs for the same miRNA in any given target correlated with high scoring hits. However, this approach failed to accurately predict single conserved sites (MREs) for miRNAs because there was no statistically significant difference between the real miRNAs versus randomized sequences (Stark et al. 2003). Stark et at presented experimental verification for six of their predicted *Drosophila* miRNA targets. Their assay monitored the miRNA-dependent downregulation of a reporter construct that contained the entire 3'-UTR from the putative miRNA target (Stark et al. 2003). Four of the tested targets (m4 and hairy mRNAs, targeted by miR-7; and reaper and grim mRNAs, targeted by miR-2) were predicted to harbor only a single site for their cognate miRNAs (Stark et al. 2003) and repressed the levels of the reporter. FIG. 6C shows the putative base-pairing between these four targets and their cognate miRNAs. Three of these target:miRNA interactions (reaper:miR-2a, grim:miR-2a and m4:miR-7) abide by the miRNA binding rules (and in particular the configuration □ shown in FIG. 5A). The hairy:miR-7 interaction (as depicted in (Stark et al. 2003); and see left side of FIG. 6C) does not, at first inspection, seem to abide by our miRNA binding rules. A closer analysis, however, shows that an alternative configuration between hairy and miR-7 may be adopted (see FIG. 6C, right side), which does abide by the miRNA binding rules (and in particular the configuration α shown in FIG. 5A). An experimentally validated miRNA target that does not contain MREs that follow the miRNA binding rules, is the *Drosophila* hid mRNA that is regulated by the bantam miRNA (Brennecke et al. 2003). We note that hid mRNA contains multiple sites that show partial complementarity, especially with the proximal region, of bantam. We expect that the miRNA binding rules are more "lax" if multiple MREs are present in the 3'-UTR of target genes. In such cases the cumulative effect of many "weaker" miRNA:MRE interactions may lead to robust repression of target gene expression. Indeed, cooperativity of multiple MREs has been demonstrated (Ha et al. 1996) (Doench et al. 2003). Similarly, most of the predicted targets for *Drosophila* (Enright et al. 2003; Stark et al. 2003) and mammalian (Lewis et al. 2003) miRNAs, contain multiple MREs; in that case the most critical aspect of miRNA:target RNA interactions, is perfect base-pairing between the proximal region of miRNAs and their targets (Stark et al. 2003) (Lewis et al. 2003).

Bartel, Burge and colleagues have presented a computational algorithm that allows prediction of conserved, mammalian miRNA targets along with accurate estimates of false positive rates and experimental validation of 11 (out of 15 tested) predicted targets (Lewis et al. 2003). The targets identified by Lewis et al. contain multiple MREs for the same miRNA or are regulated by more that one miRNA and are very different from the ones that we report. The targets reported for *Drosophila* miRNAs also contain, mostly, multiple MREs (Stark et al. 2003) (Enright et al. 2003). In contrast, our study uncovers predominantly targets that contain single MREs. This is due to the different strategies employed and underscores the importance of using multiple independent approaches to uncover the full gamut of miRNA targets. Our approach is based on the experimental deduction of rules by evaluating the significance of individual miRNA bases on target RNA recognition. Our validation assay for putative MREs utilizes a single MRE in the 3'-UTR of the RL reporter, which is under the control of the relatively strong Herpes simplex thymidine kinase promoter. We deliberately chose to insert a single MRE to avoid extraneous effects of longer sequences that may have arisen if multiple MRE copies or if the entire 3'-UTR of the target genes were used. At the same time, our assay may not be sensitive enough to detect "weaker" miRNA:MRE interactions that may become apparent when multiple MREs are used. This may be true for miRNAs that are expressed at low levels or for "low-affinity" miRNA:MRE interactions. Many miRNAs are surprisingly abundant (Lim et al. 2003) and we expect that a single MRE should suffice to detect "high affinity" miRNA:MRE interactions. As a result, our rules predict miRNA targets that contain, in the vast majority of cases, single MREs. In contrast, the computational approaches employed by (Lewis et al. 2003), (Stark et al. 2003) and (Enright et al. 2003) were geared towards identifying targets containing multiple MREs.

An important point that emerges from this study and that of (Lewis et al. 2003), and (Stark et al. 2003), is the significance of the 5'-end of the miRNA for target RNA recognition. The manner by which the remainder of the miRNA base-pairs with its target becomes more important in cases where a single MRE is used. It is also becoming apparent that, in general, miRNAs recognize more targets containing multiple MREs (Lewis et al. 2003), (Stark et al. 2003) (Enright et al. 2003) rather than single MREs (as shown in this study). However, we note that additional miRNA binding rules (for miRNAs recognizing single MREs) are likely to exist and the putative targets that we propose may represent just a fraction of the total number of targets bearing single MREs.

Materials & Methods

Computational Analysis

The computational analysis included the use of the program DIANA-microT which is accessible at http//diana.pcbi.upenn.edu/DIANA-microT, which is incorporated herein by reference.

Plasmids and siRNAs

MREs (sequences were cloned in the 3'-UTR of the pRL-TK vector (coding for *Renilla* Luciferase; Promega), embedded in a common DNA backbone containing sites for the restriction enzymes: XbaI, NdeI, XhoI and NotI. Briefly, for each MRE, two complementary DNA oligos were synthesized (sense: 5'-CTA GAG ACT AAA TGA CTC CAT ATG ACA sense MRE ACG CTC GAG GC-3'; antisense: 5'-GGC CGC CTC GAG CGT antisense MRE TGT CAT ATG GAG TCA TTT AGT CT-3'), annealed and cloned in the XbaI-NotI sites of the pRL-TK vector. Sequences of siRNA duplexes were: let-7b-M1, antisense: 5'-UGA GGG UAG UAG GUU GUG UGG U, sense: 5'-CAC ACA ACC UAC UAC CCU CAU U; let-7b-M4, antisense: 5'-UGA GGC UAG UAG GUU GUG UGG U, sense: 5'-CAC ACA ACC UAC UAG CCU CAU U.

Transfections, Dual Luciferase Assays and Northern Blots pRL-TK plasmids bearing MREs in the 3'-UTR, (0.4 μg) were cotransfected along with PGL-3 reporter plasmid (coding for Firefly Luciferase; Promega –0.4 μg-) into HeLa S3 cells (~×10$^5$) using Lipofectamine 2000 (Invitrogen). Luciferase activities were determined using Dual Luciferase Reporter Assay System (Promega). For siRNA transfections, 30 nM of each siRNA duplex was transfected using Lipofectamine 2000.

For Northern blots, HeLa cells (~1×10$^6$) were cotransfected with pRL-TK-LIN-28 or pRL-TK-M1 plasmids (2 μg) and pGL3 plasmid (2 μg) in 6-well plates. 18 hrs after transfection total cell lysates were assayed for luciferase activities and RNA was isolated. To control for transfection efficiency, samples with the same firefly luminescence values were used. Total RNA (10 μg) from each sample was fractionated on a 1% formaldehyde-agarose gel, transferred to a Nylon membrane (Amersham) and probed with [α-$^{32}$P]-dCTP-labeled DNA probe against *Renilla* Luciferase. After autoradiography, the blot was stripped and reprobed with a radiolabeled probe against β-actin (Ambion). Probes were labeled with a random primed DNA labeling kit from Roche.

Example 2

Identification of MRE and Generation of miRNA Sequence

An mRNA sequence is chosen and an MRE is identified using the methods described in the previous methods. An miRNA sequence is generated that satisfies the rules described herein. The miRNA sequence is 22 nucleobases in length and is XX complementary to the mRNA. The miRNA is synthesized and tested for its ability to modulate the expression of the mRNA. The miRNA is found to inhibit the expression of the mRNA.

REFERENCES

The references herein and sequences referred to herein by GENBANK Accession numbers are hereby incorporated herein by reference in their entirety.

Abrahante J E, D. A., Li M, Volk M L, Tennessen J M, Miller E A, Rougvie A E. 2003. The *Caenorhabditis elegans* hunchback-like Gene lin-57/hbl-1 Controls Developmental Time and Is Regulated by MicroRNAs. *Dev Cell* 4: 625-37.

Amarzguioui, M., T. Holen, E. Babaie, and H. Prydz. 2003. Tolerance for mutations and chemical modifications in a siRNA. Nucleic Acids Res 31: 589-95.

Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun, and T. Tuschl. 2003a. A uniform system for microRNA annotation. *Rna* 9: 277-9.

Ambros, V., R. C. Lee, A. Lavanway, P. T. Williams, and D. Jewell. 2003b. MicroRNAs and Other Tiny Endogenous RNAs in *C. elegans*. *Curr Biol* 13: 807-18.

Aukerman, M. J. and H. Sakai. 2003. Regulation of Flowering Time and Floral Organ Identity by a MicroRNA and Its APETALA2-Like Target Genes. *Plant Cell* 15: 2730-41.

Bartel, B. and D. P. Bartel. 2003. MicroRNAs: At the Root of Plant Development? *Plant Physiol* 132: 709-17.

Bartel, D. P. 2004. MicroRNAs: genomics, biogenesis, mechanism, and function. *Cell* 116: 281-97.

Bernstein, E., A. A. Caudy, S. M. Hammond, and G. J. Hannon. 2001. Role for a bidentate ribonuclease in the initiation step of RNA interference. *Nature* 409: 363-6.

Bohnsack, M. T., K. Czaplinski, and D. Gorlich. 2004. Exportin 5 is a RanGTP-dependent dsRNA-binding protein that mediates nuclear export of pre-miRNAs. *Rna* 10: 185-91.

Brennecke, J., D. R. Hipfner, A. Stark, R. B. Russell, and S. M. Cohen. 2003. bantam Encodes a Developmentally Regulated microRNA that Controls Cell Proliferation and Regulates the Proapoptotic Gene hid in Drosophila. *Cell* 113: 25-36.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich, and C. M. Croce. 2002. Frequent deletions and down-regulation of micro RNA genes miR15 and miR16 at 13q14 in chronic lymphocytic leukemia. *Proc Natl Acad Sci USA* 99: 15524-9.

Chen, H. 2004. A microRNA as a translational repressor of APETALA2 in Arabidopsis Flower Development. *Science* 303: 2022-25.

Doench, J. G., C. P. Petersen, and P. A. Sharp. 2003. siRNAs can function as miRNAs. *Genes Dev* 17: 438-42.

Doench, J. G. and P. A. Sharp. 2004. Specificity of microRNA target selection in translational repression. *Genes Dev* 18: 504-11.

Dostie, J., Z. Mourelatos, M. Yang, A. Sharma, and G. Dreyfuss. 2003. Numerous microRNPs in neuronal cells containing novel microRNAs. *Rna* 9: 180-186.

Elbashir, S. M., W. Lendeckel, and T. Tuschl. 2001. RNA interference is mediated by 21- and 22-nucleotide RNAs. Genes Dev 15: 188-200.

Enright, A. J., J. Bino, U. Gaul, T. Tuschl, C. Sander, and D. S. Marks. 2003. MicroRNA targets in *Drosophila*. *Genome Biology* 5.

Grishok, A., A. E. Pasquinelli, D. Conte, N. Li, S. Parrish, I. Ha, D. L. Baillie, A. Fire, G. Ruvkun, and C. C. Mello. 2001. Genes and mechanisms related to RNA interference regulate expression of the small temporal RNAs that control *C. elegans* developmental timing. *Cell* 106: 23-34.

Ha, I., B. Wightman, and G. Ruvkun. 1996. A bulged lin-4/lin-14 RNA duplex is sufficient for *Caenorhabditis elegans* lin-14 temporal gradient formation. *Genes Dev* 10: 3041-50.

Hamilton, A. J. and D. C. Baulcombe. 1999. A species of small antisense RNA in posttranscriptional gene silencing in plants. *Science* 286: 950-2.

Hammond, S. M., S. Boettcher, A. A. Caudy, R. Kobayashi, and G. J. Hannon. 2001. Argonaute2, a link between genetic and biochemical analyses of RNAi. *Science* 293: 1146-50.

Hutvagner, G., J. McLachlan, A. E. Pasquinelli, E. Balint, T. Tuschl, and P. D. Zamore. 2001. A cellular function for the RNA-interference enzyme Dicer in the maturation of the let-7 small temporal RNA. *Science* 293: 834-8.

Hutvagner, G. and P. D. Zamore. 2002. A microRNA in a multiple-turnover RNAi enzyme complex. *Science* 297: 2056-60.

Kasprzyk, A., D. Keefe, D. Smedley, D. London, W. Spooner, C. Melsopp, M. Hammond, P. Rocca-Serra, T. Cox, and E. Birney. 2004. EnsMart: a generic system for fast and flexible access to biological data. *Genome Res* 14: 160-9.

Kasschau, K. D., Z. Xie, E. Allen, C. Llave, E. J. Chapman, K. A. Krizan, and J. C. Carrington. 2003. P1/HC-Pro, a viral suppressor of RNA silencing, interferes with Arabidopsis development and miRNA unction. *Dev Cell* 4: 205-17.

Ketting, R. F., S. E. Fischer, E. Bernstein, T. Sijen, G. J. Hannon, and R. H. Plasterk. 2001. Dicer functions in RNA interference and in synthesis of small RNA involved in developmental timing in *C. elegans*. *Genes Dev* 15: 2654-9.

Khvorova, A., A. Reynolds, and S. D. Jayasena. 2003. Functional siRNAs and miRNAs exhibit strand bias. *Cell* 115: 209-16.

Knight, S. W. and B. L. Bass. 2001. A role for the RNase III enzyme DCR-1 in RNA interference and germ line development in *Caenorhabditis elegans*. *Science* 293: 2269-71.

Lagos-Quintana, M., R. Rauhut, W. Lendeckel, and T. Tuschl. 2001. Identification of novel genes coding for small expressed RNAs. *Science* 294: 853-8.

Lagos-Quintana, M., R. Rauhut, A. Yalcin, J. Meyer, W. Lendeckel, and T. Tuschl. 2002. Identification of tissue-specific microRNAs from mouse. *Curr Biol* 12: 735-9.

Lai, E. C. 2002. Micro RNAs are complementary to 3' UTR sequence motifs that mediate negative post-transcriptional regulation. *Nat Genet* 30: 363-4.

Lau, N. C., L. P. Lim, E. G. Weinstein, and D. P. Bartel. 2001. An abundant class of tiny RNAs with probable regulatory roles in *Caenorhabditis elegans*. *Science* 294: 858-62.

Lee, R. C. and V. Ambros. 2001. An extensive class of small RNAs in *Caenorhabditis elegans*. *Science* 294: 862-4.

Lee, R. C., R. L. Feinbaum, and V. Ambros. 1993. The *C. elegans* heterochronic gene lin-4 encodes small RNAs with antisense complementarity to lin-14. *Cell* 75: 843-54.

Lee, Y., C. Ahn, J. Han, H. Choi, J. Kim, J. Yim, J. Lee, P. Provost, O. Radmark, S. Kim, and V. N. Kim. 2003. The nuclear RNase III Drosha initiates microRNA processing. Nature 425: 415-9.

Lewis, B. P., I. H. Shih, M. W. Jones-Rhoades, D. P. Bartel, and C. B. Burge. 2003. Prediction of mammalian microRNA targets. *Cell* 115: 787-98.

Lim, L. P., N. C. Lau, E. G. Weinstein, A. Abdelhakim, S. Yekta, M. W. Rhoades, C. B. Burge, and D. P. Bartel. 2003. The microRNAs of *Caenorhabditis elegans*. *Genes Dev* 17: 991-1008.

Lin S Y, J. S., Abraham M, Vella M C, Pasquinelli A, Gamberi C, Gottlieb E, Slack F J. 2003. The *C. elegans* hunchback Homolog, hbl-1, Controls Temporal Patterning and Is a Probable MicroRNA Target. *Dev Cell* 4: 639-50.

Llave, C., Z. Xie, K. D. Kasschau, and J. C. Carrington. 2002. Cleavage of Scarecrow-like mRNA targets directed by a class of Arabidopsis miRNA. *Science* 297: 2053-6.

Lund, E., S. Guttinger, A. Calado, J. E. Dahlberg, and U. Kutay. 2004. Nuclear export of microRNA precursors. *Science* 303: 95-8.

Martinez, J., A. Patkaniowska, H. Urlaub, R. Luhrmann, and T. Tuschl. 2002. Single-stranded antisense siRNAs guide target RNA cleavage in RNAi. *Cell* 110: 563-74.

Mazumder, B., V. Seshadri, and P. L. Fox. 2003. Translational control by the 3'-UTR: the ends specify the means. *Trends Biochem Sci* 28: 91-8.

Michael, M. Z., O. C. SM, N. G. van Hoist Pellekaan, G. P. Young, and R. J. James. 2003. Reduced accumulation of specific microRNAs in colorectal neoplasia. *Mol Cancer Res* 1: 882-91.

Moss, E. G., R. C. Lee, and V. Ambros. 1997. The cold shock domain protein LIN-28 controls developmental timing in *C. elegans* and is regulated by the lin-4 RNA. *Cell* 88: 637-46.

Moss, E. G. and L. Tang. 2003. Conservation of the heterochronic regulator Lin-28, its developmental expression and microRNA complementary sites. *Dev Biol* 258: 432-42.

Mourelatos, Z., J. Dostie, S. Paushkin, A. Sharma, B. Charroux, L. Abel, J. Rappsilber, M. Mann, and G. Dreyfuss. 2002. miRNPs: a novel class of ribonucleoproteins containing numerous microRNAs. *Genes Dev* 16: 720-8.

Nelson, P., M. Kiriakidou, A. Sharma, E. Maniataki, and Z. Mourelatos. 2003. The microRNA world: small is mighty. *Trends Biochemical Science* 28: 534-540.

Nelson, P. T., A. G. Hatzigeorgiou, and Z. Mourelatos. 2004. miRNP:mRNA association in polyribosomes in a human neuronal cell line. *Rna* 10: 387-394.

Nussinov, R. 1981. Nearest neighbor nucleotide patterns. Structural and biological implications. *J Biol Chem* 256: 8458-62.

Olsen, P. H. and V. Ambros. 1999. The lin-4 regulatory RNA controls developmental timing in *Caenorhabditis elegans* by blocking LIN-14 protein synthesis after the initiation of translation. *Dev Biol* 216: 671-80.

Palatnik, J. F., E. Allen, X. Wu, C. Schommer, R. Schwab, J. C. Carrington, and D. Weigel. 2003. Control of leaf morphogenesis by microRNAs. *Nature* 425: 257-63.

Pesole, G., S. Liuni, G. Grillo, F. Licciulli, F. Mignone, C. Gissi, and C. Saccone. 2002. UTRdb and UTRsite: specialized databases of sequences and functional elements of 5' and 3' untranslated regions of eukaryotic mRNAs. Update 2002. *Nucleic Acids Res* 30: 335-40.

Pruitt, K. D., T. Tatusova, and D. R. Maglott. 2003. NCBI Reference Sequence project: update and current status. *Nucleic Acids Res* 31: 34-7.

Reinhart, B. J., F. J. Slack, M. Basson, A. E. Pasquinelli, J. C. Bettinger, A. E. Rougvie, H. R. Horvitz, and G. Ruvkun. 2000. The 21-nucleotide let-7 RNA regulates developmental timing in *Caenorhabditis elegans*. *Nature* 403: 901-6.

Rhoades, M. W., B. J. Reinhart, L. P. Lim, C. B. Burge, B. Bartel, and D. P. Bartel. 2002. Prediction of plant microRNA targets. *Cell* 110: 513-20.

Schwarz, D. S., G. Hutvagner, T. Du, Z. Xu, N. Aronin, and P. D. Zamore. 2003. Asymmetry in the assembly of the RNAi enzyme complex. *Cell* 115: 199-208.

Seggerson, K., L. Tang, and E. G. Moss. 2002. Two genetic circuits repress the *Caenorhabditis elegans* heterochronic gene lin-28 after translation initiation. *Dev Biol* 243: 215-25.

Seitz, H., N. Youngson, S. P. Lin, S. Dalbert, M. Paulsen, J. P. Bachellerie, A. C. Ferguson-Smith, and J. Cavaille. 2003. Imprinted microRNA genes transcribed antisense to a reciprocally imprinted retrotransposon-like gene. *Nat Genet* 34: 261-2.

Stark, A., J. Brennecke, R. B. Russell, and S. M. Cohen. 2003. Identification of Drosophila MicroRNA Targets. *Plos Biology* 1: 1-13.

Tang, G., B. J. Reinhart, D. P. Bartel, and P. D. Zamore. 2003. A biochemical framework for RNA silencing in plants. *Genes Dev* 17: 49-63.

Tinoco, I. J. and e. al. 1973. *Nat New Biol* 246: 40-41.

Vella, M. C., E. Y. Choi, S. Y. Lin, K. Reinert, and F. J. Slack. 2004. The *C. elegans* microRNA let-7 binds to imperfect let-7 complementary sites from the lin-41 3'UTR. *Genes Dev* 18: 132-7.

Wightman, B., 1. Ha, and G. Ruvkun. 1993. Posttranscriptional regulation of the heterochronic gene lin-14 by lin-4 mediates temporal pattern formation in *C. elegans*. *Cell* 75: 855-62.

Xie, Z., K. D. Kasschau, and J. C. Carrington. 2003. Negative Feedback Regulation of Dicer-Like1 in Arabidopsis by microRNA-Guided mRNA Degradation. *Curr Biol* 13: 784-9.

Xu, P., S. Y. Vernooy, M. Guo, and B. A. Hay. 2003. The *Drosophila* MicroRNA Mir-14 Suppresses Cell Death and Is Required for Normal Fat Metabolism. *Curr Biol* 13: 790-5.

Yi, R., Y. Qin, I. G. Macara, and B. R. Cullen. 2003. Exportin-5 mediates the nuclear export of pre-microRNAs and short hairpin RNAs. *Genes Dev* 17: 3011-6.

Zeng, Y., E. J. Wagner, and B. R. Cullen. 2002. Both natural and designed micro RNAs can inhibit the expression of cognate mRNAs when expressed in human cells. *Mol Cell* 9: 1327-33.

The invention claimed is:

1. A system for identifying a microRNA-recognition element comprising:

an input interface for inputting mRNA sequences, a database of mRNA sequences or a link for connecting to a remote data input interface, data or a database of mRNA sequences;

an input interface for inputting microRNA sequences, a database of microRNA sequences or a link for connecting to a remote data input interface, data or a database of microRNA sequences;

a processor with instructions for comparing mRNA sequences to microRNA sequences to identify a microRNA-recognition element by:

comparing degree of complementarity of a microRNA nucleotide sequence to an mRNA sequence to identify the presence of an mRNA sequence that exhibits a degree of complementarity to the microRNA sequence that is indicative of a microRNA-recognition element for the microRNA, wherein the microRNA is 17-25 nucleotides and includes a proximal region that is 7-9 nucleotides, has a 5' end and a 3' end and includes a nucleotide at the 5' end which is the microRNA's 5' terminus nucleotide, a distal region that is 7-15 nucleotides, has a 5' end and a 3' end and includes a nucleotide at the 3' end which is the microRNA's 3' terminus nucleotide, and a loop region that is 0 nucleotide, 2-3 nucleotides or 6-9 nucleotide, wherein when the loop region is 0 nucleotides the 3' end of the proximal region is contiguous to the 5' end of the distal region and when the loop region is 2-3 or 6-9 nucleotides the 3' end of the proximal region is contiguous to the 5' end of the loop region and the 3' end of the loop region is contiguous to the 5' end of the distal region, wherein complementarity of the mRNA sequence to the microRNA sequence that is indicative of a microRNA-response element for the microRNA is characterized by:

an mRNA sequence having a sequence that:

a) includes a region corresponding to the proximal region of the microRNA that is either completely complementary to the proximal region, or has a single mismatch to the 5' end of the proximal region, or symmetrically placed between the 5' end of the proximal region and the 3' end of the proximal region;

b) includes a region corresponding to the loop region of the microRNA that either forms a loop of 2-5 non-paired nucleotides when the loop region is 0, or has 0 nucleotides when the loop region is 6-9 nucleotides, or has 2-3 nucleotides which forms a bulge of 2-3 non-complementary nucleotides of the loop region when the loop region is 2-3 nucleotides; and c) includes a region corresponding to the distal region that is either completely complementary to at least 7 contiguous nucleotides of the distal region including the 5' end of the distal region, or contains mismatches of 1-4 contiguous nucleotides and matches of at least 5 nucleotides to a contiguous nucleotide sequence of the distal region including the 5' end of the distal region;

wherein an mRNA sequence that has complementarity to the microRNA sequence that is indicative of a microRNA-recognition element for the microRNA indicates that said mRNA sequence is a microRNA-recognition element for the microRNA.

2. The system of claim 1 comprising a link for connecting to a database of mRNA sequences.

3. The system of claim 1 comprising an input interface for inputting microRNA sequences.

4. A computer program embodied on a computer readable medium for implementation on a computer system that for identifying a microRNA-recognition element, the program comprising instructions for performing the following steps:

comparing degree of complementarity of a microRNA nucleotide sequence to an mRNA sequence to identify the presence of an mRNA sequence that exhibits a degree of complementarity to the microRNA sequence that is indicative of a microRNA-recognition element for the microRNA, wherein the microRNA is 17-25 nucleotides and includes a proximal region that is 7-9 nucleotides, has a 5' end and a 3' end and includes a nucleotide at the 5' end which is the microRNA's 5' terminus nucleotide, a distal region that is 7-15 nucleotides, has a 5' end and a 3' end and includes a nucleotide at the 5' end which is the microRNA's 5' terminus nucleotide, and a loop region that is 0 nucleotide, 2-3 nucleotides or 6-9 nucleotide, wherein when the loop region is 0 nucleotides the 3' end of the proximal region is contiguous to the 5' end of the distal region and when the loop region is 2-3 or 6-9 nucleotides the 3' end of the proximal region is contiguous to the 5' end of the loop region and the 3' end of the loop region is contiguous to the 5' end of the distal region, wherein complementarity of the mRNA sequence to the microRNA sequence that is indicative of a microRNA-response element for the microRNA is characterized by:

an mRNA sequence having a sequence that:

a) includes a region corresponding to the proximal region of the microRNA that is either completely complementary to the proximal region, or has a single mismatch to the 5' end of the proximal region, or symmetrically placed between the 5' end of the proximal region and the 3' end of the proximal region;

b) includes a region corresponding to the loop region of the microRNA that either forms a loop of 2-5 non-paired nucleotides when the loop region is 0, or has 0 nucleotides when the loop region is 6-9 nucleotides, or has 2-3 nucleotides which forms a bulge of 2-3 non-complementary nucleotides of the loop region when the loop region is 2-3 nucleotides; and c) includes a region corresponding to the distal region that is either completely complementary to at least 7 contiguous nucleotides of the distal region including the 5' end of the distal region, or contains mismatches of 1-4 contiguous nucleotides and matches of at least 5 nucleotides to a contiguous nucleotide sequence of the distal region including the 5' end of the distal region;

wherein an mRNA sequence that has complementarity to the microRNA sequence that is indicative of a microRNA-recognition element for the microRNA indicates that said mRNA sequence is a microRNA-recognition element for the microRNA.

* * * * *

SEQUENCE LISTING

```
<160> NUMBER OF SEQ ID NOS: 83

<210> SEQ ID NO 1
<211> LENGTH: 22
<212> TYPE: RNA
<213> ORGANISM: Artificial Sequence
<220> FEATURE:
<223> OTHER INFORMATION: LIN-41a microRNA recognition element

<400> SEQUENCE: 1
uuauacaacc guucuacacu ca                                                  22

<210> SEQ ID NO 2
<211> LENGTH: 22
<212> TYPE: RNA
<213> ORGANISM: Homo sapiens

<400> SEQUENCE: 2
ugagguagua gguuguauag uu                                                  22

<210> SEQ ID NO 3
<211> LENGTH: 20
<212> TYPE: RNA
<213> ORGANISM: Artificial Sequence
<220> FEATURE:
<223> OTHER INFORMATION: LIN-41b microRNA recognition element

<400> SEQUENCE: 3
uuauacaacc auucugccuc                                                     20

<210> SEQ ID NO 4
<211> LENGTH: 23
<212> TYPE: RNA
<213> ORGANISM: Artificial Sequence
<220> FEATURE:
<223> OTHER INFORMATION: LIN-28, wt microRNA recognition element

<400> SEQUENCE: 4
gcacagccua uugaacuacc uca                                                 23

<210> SEQ ID NO 5
<211> LENGTH: 22
<212> TYPE: RNA
<213> ORGANISM: Homo sapiens

<400> SEQUENCE: 5
ugagguagua gguugugugg uu                                                  22

<210> SEQ ID NO 6
<211> LENGTH: 24
<212> TYPE: RNA
<213> ORGANISM: Artificial Sequence
<220> FEATURE:
<223> OTHER INFORMATION: LIN-28, M1 microRNA recognition element

<400> SEQUENCE: 6
```

-continued gcacagccua uugaacuacc guca                                           24

<210> SEQ ID NO 7
<211> LENGTH: 22
<212> TYPE: RNA
<213> ORGANISM: Artificial Sequence
<220> FEATURE:
<223> OTHER INFORMATION: LIN-28, M2 microRNA recognition element

<400> SEQUENCE: 7
gcacagccua uugaacuacu ca                                             22

<210> SEQ ID NO 8
<211> LENGTH: 24
<212> TYPE: RNA
<213> ORGANISM: Artificial Sequence
<220> FEATURE:
<223> OTHER INFORMATION: LIN-28, M3 microRNA recognition element

<400> SEQUENCE: 8
gcacagccua uugaacuaca cuca                                           24

<210> SEQ ID NO 9
<211> LENGTH: 24
<212> TYPE: RNA
<213> ORGANISM: Artificial Sequence
<220> FEATURE:
<223> OTHER INFORMATION: LIN-28, M4 microRNA recognition element

<400> SEQUENCE: 9
gcacagccua uugaacuagc cuca                                           24

<210> SEQ ID NO 10
<211> LENGTH: 24
<212> TYPE: RNA
<213> ORGANISM: Artificial Sequence
<220> FEATURE:
<223> OTHER INFORMATION: LIN-28, M5 microRNA recognition element

<400> SEQUENCE: 10
gcacagccua uugaacuuac cuca                                           24

<210> SEQ ID NO 11
<211> LENGTH: 24
<212> TYPE: RNA
<213> ORGANISM: Artificial Sequence
<220> FEATURE:
<223> OTHER INFORMATION: LIN-28, M6 microRNA recognition element

<400> SEQUENCE: 11
gcacagccua uugaacauac cuca                                           24

<210> SEQ ID NO 12
<211> LENGTH: 24
<212> TYPE: RNA
<213> ORGANISM: Artificial Sequence
<220> FEATURE:
<223> OTHER INFORMATION: LIN-28, M7 microRNA recognition element

<400> SEQUENCE: 12
gcacagccuu auugaacuac cuca                                           24

<210> SEQ ID NO 13
<211> LENGTH: 24
<212> TYPE: RNA
<213> ORGANISM: Artificial Sequence
<220> FEATURE:

<223> OTHER INFORMATION: LIN-28, M8 microRNA recognition element

<400> SEQUENCE: 13
gcacagccau auugaacuac cuca                        24

<210> SEQ ID NO 14
<211> LENGTH: 24
<212> TYPE: RNA
<213> ORGANISM: Artificial Sequence
<220> FEATURE:
<223> OTHER INFORMATION: LIN-28, M9 microRNA recognition element

<400> SEQUENCE: 14
gcacagcacu auugaacuac cuca                        24

<210> SEQ ID NO 15
<211> LENGTH: 24
<212> TYPE: RNA
<213> ORGANISM: Artificial Sequence
<220> FEATURE:
<223> OTHER INFORMATION: LIN-28, M10 microRNA recognition element

<400> SEQUENCE: 15
gcaacagccu auugaacuac cuca                        24

<210> SEQ ID NO 16
<211> LENGTH: 23
<212> TYPE: RNA
<213> ORGANISM: Artificial Sequence
<220> FEATURE:
<223> OTHER INFORMATION: LIN-28, M11 microRNA recognition element

<400> SEQUENCE: 16
gcacagccua uugaccuacc uca                         23

<210> SEQ ID NO 17
<211> LENGTH: 20
<212> TYPE: RNA
<213> ORGANISM: Artificial Sequence
<220> FEATURE:
<223> OTHER INFORMATION: LIN-28, M12 microRNA recognition element

<400> SEQUENCE: 17
gcacagccua gacuaccuca                             20

<210> SEQ ID NO 18
<211> LENGTH: 21
<212> TYPE: RNA
<213> ORGANISM: Artificial Sequence
<220> FEATURE:
<223> OTHER INFORMATION: LIN-28, M13 microRNA recognition element

<400> SEQUENCE: 18
gcacagccua gaacuaccuc a                           21

<210> SEQ ID NO 19
<211> LENGTH: 22
<212> TYPE: RNA
<213> ORGANISM: Artificial Sequence
<220> FEATURE:
<223> OTHER INFORMATION: LIN-28, M14 microRNA recognition element

<400> SEQUENCE: 19
gcacagccua ugaacuaccu ca                          22

<210> SEQ ID NO 20

```
<211> LENGTH: 24
<212> TYPE: RNA
<213> ORGANISM: Artificial Sequence
<220> FEATURE:
<223> OTHER INFORMATION: LIN-28, M15 microRNA recognition element

<400> SEQUENCE: 20
gcacagccua cuugaacuac cuca                                          24

<210> SEQ ID NO 21
<211> LENGTH: 25
<212> TYPE: RNA
<213> ORGANISM: Artificial Sequence
<220> FEATURE:
<223> OTHER INFORMATION: LIN-28, M16 microRNA recognition element

<400> SEQUENCE: 21
gcacagccua gcuugaacua ccuca                                         25

<210> SEQ ID NO 22
<211> LENGTH: 12
<212> TYPE: RNA
<213> ORGANISM: Artificial Sequence
<220> FEATURE:
<223> OTHER INFORMATION: LIN-28, M17 microRNA recognition element

<400> SEQUENCE: 22
accacuaccu ca                                                       12

<210> SEQ ID NO 23
<211> LENGTH: 14
<212> TYPE: RNA
<213> ORGANISM: Artificial Sequence
<220> FEATURE:
<223> OTHER INFORMATION: LIN-28, M18 microRNA recognition element

<400> SEQUENCE: 23
accacacuac cuca                                                     14

<210> SEQ ID NO 24
<211> LENGTH: 16
<212> TYPE: RNA
<213> ORGANISM: Artificial Sequence
<220> FEATURE:
<223> OTHER INFORMATION: LIN-28, M19 microRNA recognition element

<400> SEQUENCE: 24
accacacacu accuca                                                   16

<210> SEQ ID NO 25
<211> LENGTH: 18
<212> TYPE: RNA
<213> ORGANISM: Artificial Sequence
<220> FEATURE:
<223> OTHER INFORMATION: LIN-28, M20 microRNA recognition element

<400> SEQUENCE: 25
accacacaua cuaccuca                                                 18

<210> SEQ ID NO 26
<211> LENGTH: 19
<212> TYPE: RNA
<213> ORGANISM: Artificial Sequence
<220> FEATURE:
<223> OTHER INFORMATION: LIN-28, M21 microRNA recognition element

<400> SEQUENCE: 26
```
accacacaau acuaccuca                                                      19

<210> SEQ ID NO 27
<211> LENGTH: 22
<212> TYPE: RNA
<213> ORGANISM: Artificial Sequence
<220> FEATURE:
<223> OTHER INFORMATION: let-7b-M1 synthetic MicroRNA

<400> SEQUENCE: 27
ugaggguagu agguugugug gu                                                  22

<210> SEQ ID NO 28
<211> LENGTH: 22
<212> TYPE: RNA
<213> ORGANISM: Artificial Sequence
<220> FEATURE:
<223> OTHER INFORMATION: let-7b-M4 synthetic MicroRNA

<400> SEQUENCE: 28
ugaggcuagu agguugugug gu                                                  22

<210> SEQ ID NO 29
<211> LENGTH: 19
<212> TYPE: RNA
<213> ORGANISM: Artificial Sequence
<220> FEATURE:
<223> OTHER INFORMATION: CLOCK microRNA recognition element

<400> SEQUENCE: 29
agccaguucu gacaguguu                                                      19

<210> SEQ ID NO 30
<211> LENGTH: 23
<212> TYPE: RNA
<213> ORGANISM: Homo sapiens

<400> SEQUENCE: 30
aacacugucu gguaaagaug gcu                                                 23

<210> SEQ ID NO 31
<211> LENGTH: 18
<212> TYPE: RNA
<213> ORGANISM: Artificial Sequence
<220> FEATURE:
<223> OTHER INFORMATION: MAPK14 microRNA recognition element

<400> SEQUENCE: 31
cugcugaagu ucugagcc                                                       18

<210> SEQ ID NO 32
<211> LENGTH: 22
<212> TYPE: RNA
<213> ORGANISM: Homo sapiens

<400> SEQUENCE: 32
uggcucaguu cagcaggaac ag                                                  22

<210> SEQ ID NO 33
<211> LENGTH: 22
<212> TYPE: DNA
<213> ORGANISM: Artificial Sequence
<220> FEATURE:
<223> OTHER INFORMATION: fragment of human actin gamma - top string
      let-7b binding site

<400> SEQUENCE: 33

```
cacacacctc atgctagcct ca                                                22
```

<210> SEQ ID NO 34
<211> LENGTH: 19
<212> TYPE: DNA
<213> ORGANISM: Artificial Sequence
<220> FEATURE:
<223> OTHER INFORMATION: fragment of human actin gamma - bottom string
      let-7b binding site

<400> SEQUENCE: 34

```
tgaggtagta ggttgtgtg                                                    19
```

<210> SEQ ID NO 35
<211> LENGTH: 23
<212> TYPE: DNA
<213> ORGANISM: Artificial Sequence
<220> FEATURE:
<223> OTHER INFORMATION: fragment of human ribose 5-phosphate isomerase
      A - top string let-7b binding site

<400> SEQUENCE: 35

```
cacagccaag gtggacgtac ctc                                               23
```

<210> SEQ ID NO 36
<211> LENGTH: 19
<212> TYPE: DNA
<213> ORGANISM: Artificial Sequence
<220> FEATURE:
<223> OTHER INFORMATION: fragment of human ribose 5-phosphate isomerase
      A - bottom string let-7b binding site

<400> SEQUENCE: 36

```
gaggtagtag gttgtgtgg                                                    19
```

<210> SEQ ID NO 37
<211> LENGTH: 21
<212> TYPE: DNA
<213> ORGANISM: Artificial Sequence
<220> FEATURE:
<223> OTHER INFORMATION: fragment of human eucaryotic translation
      initiation factor 3, submit 1 alpha - top string let-7e binding
      site

<400> SEQUENCE: 37

```
atacagcctt aaccatacct c                                                 21
```

<210> SEQ ID NO 38
<211> LENGTH: 17
<212> TYPE: DNA
<213> ORGANISM: Artificial Sequence
<220> FEATURE:
<223> OTHER INFORMATION: fragment of human eucaryotic translation
      initiation factor 3, submit 1 alpha - bottom string let-7e binding
      site

<400> SEQUENCE: 38

```
gaggtaggag gttgtat                                                      17
```

<210> SEQ ID NO 39
<211> LENGTH: 17
<212> TYPE: DNA
<213> ORGANISM: Artificial Sequence
<220> FEATURE:
<223> OTHER INFORMATION: fragment of human chromosome 22 open reading
      frame 5 - top string miR-15 binding site

<400> SEQUENCE: 39

```
caggccaaag tgctgct                                                     17
```

<210> SEQ ID NO 40
<211> LENGTH: 21
<212> TYPE: DNA
<213> ORGANISM: Artificial Sequence
<220> FEATURE:
<223> OTHER INFORMATION: fragment of human chromosome 22 open reading
      frame 5 - bottom string miR-15 binding site

<400> SEQUENCE: 40

```
agcagcacat aatggtttgt g                                                21
```

<210> SEQ ID NO 41
<211> LENGTH: 25
<212> TYPE: DNA
<213> ORGANISM: Artificial Sequence
<220> FEATURE:
<223> OTHER INFORMATION: fragment of human vascular endothelial growth
      factor - top string  miR-16 binding site

<400> SEQUENCE: 41

```
cgccatttta tttttcttgc tgcta                                            25
```

<210> SEQ ID NO 42
<211> LENGTH: 22
<212> TYPE: DNA
<213> ORGANISM: Artificial Sequence
<220> FEATURE:
<223> OTHER INFORMATION: fragment of human vascular endothelial growth
      factor - bottom string miR-16 binding site

<400> SEQUENCE: 42

```
tagcagcacg taaatattgg cg                                               22
```

<210> SEQ ID NO 43
<211> LENGTH: 20
<212> TYPE: DNA
<213> ORGANISM: Artificial Sequence
<220> FEATURE:
<223> OTHER INFORMATION: fragment of human cyclin T2 (CCNT2), transcript
      variant a - top string miR-16 binding site

<400> SEQUENCE: 43

```
caatatttgt aagtgctgct                                                  20
```

<210> SEQ ID NO 44
<211> LENGTH: 21
<212> TYPE: DNA
<213> ORGANISM: Artificial Sequence
<220> FEATURE:
<223> OTHER INFORMATION: fragment of human cyclin T2 (CCNT2), transcript
      variant a - bottom string miR-16 binding site

<400> SEQUENCE: 44

```
agcagcacgt aaatattggc g                                                21
```

<210> SEQ ID NO 45
<211> LENGTH: 15
<212> TYPE: DNA
<213> ORGANISM: Artificial Sequence
<220> FEATURE:
<223> OTHER INFORMATION: fragment of human KIAA0152 gene product - top
      string miR-24 binding site

<400> SEQUENCE: 45

```
tcctgctctg agcca                                                       15
```

```
<210> SEQ ID NO 46
<211> LENGTH: 22
<212> TYPE: DNA
<213> ORGANISM: Artificial Sequence
<220> FEATURE:
<223> OTHER INFORMATION: fragment of human KIAA0152 gene product -
      bottom string miR-24 binding site

<400> SEQUENCE: 46
tggctcagtt cagcaggaac ag                                              22

<210> SEQ ID NO 47
<211> LENGTH: 17
<212> TYPE: DNA
<213> ORGANISM: Artificial Sequence
<220> FEATURE:
<223> OTHER INFORMATION: fragment of human glycerol-3-phosphate
      dehydrogenase 1 (soluable) - top string miR-103 binding site

<400> SEQUENCE: 47
tcaagcccca gtgctgc                                                    17

<210> SEQ ID NO 48
<211> LENGTH: 22
<212> TYPE: DNA
<213> ORGANISM: Artificial Sequence
<220> FEATURE:
<223> OTHER INFORMATION: fragment of human glycerol-3-phosphate
      dehydrogenase 1 (soluable) - bottom string miR-103 binding site

<400> SEQUENCE: 48
gcagcattgt acagggctat ga                                              22

<210> SEQ ID NO 49
<211> LENGTH: 23
<212> TYPE: DNA
<213> ORGANISM: Artificial Sequence
<220> FEATURE:
<223> OTHER INFORMATION: fragment of human kruppel-like factor 5
      (intestinal) - top string miR-141 (miR-157) binding site

<400> SEQUENCE: 49
ccatcattta atgtgacagt gtt                                             23

<210> SEQ ID NO 50
<211> LENGTH: 23
<212> TYPE: DNA
<213> ORGANISM: Artificial Sequence
<220> FEATURE:
<223> OTHER INFORMATION: fragment of human kruppel-like factor 5
      (intestinal) - bottom string miR-141 (miR-157) binding site

<400> SEQUENCE: 50
aacactgtct ggtaaagatg gct                                             23

<210> SEQ ID NO 51
<211> LENGTH: 17
<212> TYPE: DNA
<213> ORGANISM: Artificial Sequence
<220> FEATURE:
<223> OTHER INFORMATION: fragment of human serine/threonine kinase 3 -
      top string miR-141 (miR-157) binding site

<400> SEQUENCE: 51
gccatcttga cagtgtt                                                    17
```

-continued

```
<210> SEQ ID NO 52
<211> LENGTH: 22
<212> TYPE: DNA
<213> ORGANISM: Artificial Sequence
<220> FEATURE:
<223> OTHER INFORMATION: fragment of human serine/threonine kinase 3 -
      bottom string miR-141 (miR-157) binding site

<400> SEQUENCE: 52
aacactgtct ggtaaagatg gc                                              22

<210> SEQ ID NO 53
<211> LENGTH: 27
<212> TYPE: DNA
<213> ORGANISM: Artificial Sequence
<220> FEATURE:
<223> OTHER INFORMATION: fragment of human tropomodulin 3 (ubiquitous) -
      top string miR-145 binding site

<400> SEQUENCE: 53
ttcctgggta gagggaaaaa gactgga                                         27

<210> SEQ ID NO 54
<211> LENGTH: 17
<212> TYPE: DNA
<213> ORGANISM: Artificial Sequence
<220> FEATURE:
<223> OTHER INFORMATION: fragment of human tropomodulin 3 (ubiquitous) -
      bottom string miR-145 binding site

<400> SEQUENCE: 54
tccagttttc ccaggaa                                                    17

<210> SEQ ID NO 55
<211> LENGTH: 21
<212> TYPE: RNA
<213> ORGANISM: Artificial Sequence
<220> FEATURE:
<223> OTHER INFORMATION: fragment of human FLJ21308, microRNA
      recognition element

<400> SEQUENCE: 55
uuccucgggu ucaaagcugg a                                               21

<210> SEQ ID NO 56
<211> LENGTH: 24
<212> TYPE: RNA
<213> ORGANISM: Homo sapiens

<400> SEQUENCE: 56
guccaguuuu cccaggaauc ccuu                                            24

<210> SEQ ID NO 57
<211> LENGTH: 17
<212> TYPE: RNA
<213> ORGANISM: Artificial Sequence
<220> FEATURE:
<223> OTHER INFORMATION: fragment of human FLJ13158, microRNA
      recognition element

<400> SEQUENCE: 57
cccuggcuuu aauguga                                                    17

<210> SEQ ID NO 58
<211> LENGTH: 21
<212> TYPE: RNA
<213> ORGANISM: Homo sapiens
```

```
<400> SEQUENCE: 58
aucacauugc cagggauuuc c                                              21

<210> SEQ ID NO 59
<211> LENGTH: 18
<212> TYPE: RNA
<213> ORGANISM: Artificial Sequence
<220> FEATURE:
<223> OTHER INFORMATION: fragment of human SMC1L1, microRNA recognition
      element

<400> SEQUENCE: 59
caaccuuccc ccuaccuc                                                  18

<210> SEQ ID NO 60
<211> LENGTH: 21
<212> TYPE: RNA
<213> ORGANISM: Homo sapiens

<400> SEQUENCE: 60
ugagguagga gguuguauag u                                              21

<210> SEQ ID NO 61
<211> LENGTH: 17
<212> TYPE: RNA
<213> ORGANISM: Artificial Sequence
<220> FEATURE:
<223> OTHER INFORMATION: fragment of human hDMP1 (DMTF1), microRNA
      recognition element

<400> SEQUENCE: 61
acacauuguu gcugcua                                                   17

<210> SEQ ID NO 62
<211> LENGTH: 22
<212> TYPE: RNA
<213> ORGANISM: Homo sapiens

<400> SEQUENCE: 62
uagcagcaca uaaugguuug ug                                             22

<210> SEQ ID NO 63
<211> LENGTH: 17
<212> TYPE: RNA
<213> ORGANISM: Artificial Sequence
<220> FEATURE:
<223> OTHER INFORMATION: fragment of human CGI-38, microRNA recognition
      element

<400> SEQUENCE: 63
auauuuaagc ugcugcu                                                   17

<210> SEQ ID NO 64
<211> LENGTH: 22
<212> TYPE: RNA
<213> ORGANISM: Homo sapiens

<400> SEQUENCE: 64
uagcagcacg uaaauauugg cg                                             22

<210> SEQ ID NO 65
<211> LENGTH: 14
<212> TYPE: RNA
<213> ORGANISM: Artificial Sequence
<220> FEATURE:
<223> OTHER INFORMATION: fragment of human LAMC2, microRNA recognition
```

```
                              element

<400> SEQUENCE: 65
cagauagcac uggg                                                        14

<210> SEQ ID NO 66
<211> LENGTH: 23
<212> TYPE: RNA
<213> ORGANISM: Homo sapiens

<400> SEQUENCE: 66
cccaguguuu agacuaucug uuc                                              23

<210> SEQ ID NO 67
<211> LENGTH: 23
<212> TYPE: RNA
<213> ORGANISM: Artificial Sequence
<220> FEATURE:
<223> OTHER INFORMATION: fragment of human FBXW1B, microRNA recognition
      element

<400> SEQUENCE: 67
agcuuuguac uguggaaugu gcu                                              23

<210> SEQ ID NO 68
<211> LENGTH: 23
<212> TYPE: RNA
<213> ORGANISM: Homo sapiens

<400> SEQUENCE: 68
agcagcauug uacagggcua uga                                              23

<210> SEQ ID NO 69
<211> LENGTH: 23
<212> TYPE: RNA
<213> ORGANISM: Artificial Sequence
<220> FEATURE:
<223> OTHER INFORMATION: fragment of human LIN-28, M29 microRNA
      recognition element

<400> SEQUENCE: 69
cacacaaccu auugaacuac uca                                              23

<210> SEQ ID NO 70
<211> LENGTH: 22
<212> TYPE: RNA
<213> ORGANISM: Artificial Sequence
<220> FEATURE:
<223> OTHER INFORMATION: fragment of C. elegans lin-41 sequence,
      microRNA recognition element

<400> SEQUENCE: 70
uuauacaacc guucuacacu ca                                               22

<210> SEQ ID NO 71
<211> LENGTH: 22
<212> TYPE: RNA
<213> ORGANISM: Caenorhabditis elegans

<400> SEQUENCE: 71
ugagguagua gguuguauag uu                                               22

<210> SEQ ID NO 72
<211> LENGTH: 20
<212> TYPE: RNA
<213> ORGANISM: Artificial Sequence
```

```
<220> FEATURE:
<223> OTHER INFORMATION: fragment of C. elegans lin-41 sequence,
      microRNA recognition element 2

<400> SEQUENCE: 72
uuauacaacc auucugccuc                                                     20

<210> SEQ ID NO 73
<211> LENGTH: 15
<212> TYPE: RNA
<213> ORGANISM: Artificial Sequence
<220> FEATURE:
<223> OTHER INFORMATION: fragment of C. elegans lin-28 sequence,
      microRNA recognition element

<400> SEQUENCE: 73
uugcacucuc aggga                                                          15

<210> SEQ ID NO 74
<211> LENGTH: 21
<212> TYPE: RNA
<213> ORGANISM: Caenorhabditis elegans

<400> SEQUENCE: 74
ucccugagac cucaagugug a                                                   21

<210> SEQ ID NO 75
<211> LENGTH: 13
<212> TYPE: RNA
<213> ORGANISM: Artificial Sequence
<220> FEATURE:
<223> OTHER INFORMATION: fragment of C. elegans lin-14 sequence,
      microRNA recognition element

<400> SEQUENCE: 75
ucuaccucag gga                                                            13

<210> SEQ ID NO 76
<211> LENGTH: 21
<212> TYPE: RNA
<213> ORGANISM: Artificial Sequence
<220> FEATURE:
<223> OTHER INFORMATION: fragment of C. elegans hbl-1 sequence,
      microRNA recognition element

<400> SEQUENCE: 76
uccgcuaccu uauguaccuc a                                                   21

<210> SEQ ID NO 77
<211> LENGTH: 21
<212> TYPE: RNA
<213> ORGANISM: Caenorhabditis elegans

<400> SEQUENCE: 77
ugagguaggu gcgagaaaug a                                                   21

<210> SEQ ID NO 78
<211> LENGTH: 25
<212> TYPE: RNA
<213> ORGANISM: Artificial Sequence
<220> FEATURE:
<223> OTHER INFORMATION: fragment of the D. melanogaster hairy sequence,
      microRNA recognition element

<400> SEQUENCE: 78
acagcaaauc agcaaaaguc uucca                                               25
```

-continued

```
<210> SEQ ID NO 79
<211> LENGTH: 23
<212> TYPE: RNA
<213> ORGANISM: Drosophila melanogaster

<400> SEQUENCE: 79
uggaagacua gugauuuugu ugu                                                23

<210> SEQ ID NO 80
<211> LENGTH: 21
<212> TYPE: RNA
<213> ORGANISM: Artificial Sequence
<220> FEATURE:
<223> OTHER INFORMATION: fragment of D. melanogaster reaper sequence,
      microRNA recognition element

<400> SEQUENCE: 80
cucaucaaag cgauugugau a                                                  21

<210> SEQ ID NO 81
<211> LENGTH: 23
<212> TYPE: RNA
<213> ORGANISM: Drosophila melanogaster

<400> SEQUENCE: 81
uaucacagcc agcuuugaug agc                                                23

<210> SEQ ID NO 82
<211> LENGTH: 23
<212> TYPE: RNA
<213> ORGANISM: Artificial Sequence
<220> FEATURE:
<223> OTHER INFORMATION: fragment of D. melanogaster grim sequence,
      microRNA recognition element

<400> SEQUENCE: 82
gcucaaucaa agcgcauugu gau                                                23

<210> SEQ ID NO 83
<211> LENGTH: 22
<212> TYPE: RNA
<213> ORGANISM: Artificial Sequence
<220> FEATURE:
<223> OTHER INFORMATION: fragment of D. melanogaster m4 sequence,
      microRNA recognition element

<400> SEQUENCE: 83
cagcuuuaau caacgucuuc cg                                                 22
```